United States Patent [19]

Djuric et al.

[11] Patent Number: 4,889,871
[45] Date of Patent: Dec. 26, 1989

[54] ALKOXY-SUBSTITUTED DIHYDROBENZOPYRAN-2-CARBOXYLATE DERIVATIVES

[75] Inventors: Stevan W. Djuric, Glenview; Robert L. Shone, Palatine; Stella S. T. Yu, Morton Grove, all of Ill.

[73] Assignee: G. D. Searle & Co., Chicago, Ill.

[21] Appl. No.: 188,708

[22] Filed: May 12, 1988

Related U.S. Application Data

[63] Continuation-in-part of Ser. No. 57,136, May 29, 1987, abandoned.

[51] Int. Cl.$^4$ .................. A61K 31/35; C07D 311/66; C07D 311/58
[52] U.S. Cl. ................................ 514/456; 549/405; 549/407; 549/401; 549/402
[58] Field of Search ................ 514/456; 549/401, 402, 549/405, 407

[56] References Cited

U.S. PATENT DOCUMENTS

| | | | |
|---|---|---|---|
| 3,882,148 | 5/1975 | Augstein et al. | 549/402 |
| 4,281,008 | 7/1981 | Chamberlain et al. | 549/401 |
| 4,546,194 | 10/1985 | Miyano | 549/401 |
| 4,565,882 | 1/1983 | Miyano | 549/399 |
| 4,665,203 | 5/1987 | Miyano et al. | 549/402 |

FOREIGN PATENT DOCUMENTS

| | | |
|---|---|---|
| 0079637 | 5/1983 | European Pat. Off. |
| 0129906 | 1/1985 | European Pat. Off. |
| 62-8432 | 2/1987 | Japan |

OTHER PUBLICATIONS

Appleton et al., J. Med. Chem. 20, 371-379 (1977).

*Primary Examiner*—Nicky Chan
*Attorney, Agent, or Firm*—M. J. Kanady; P. D. Matukaitis; R. A. Williams

[57] ABSTRACT

This invention encompasses compounds of Formula 1 and the pharmaceutically acceptable salts thereof.

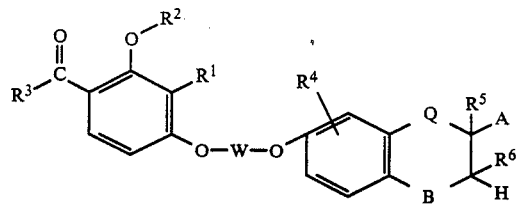

wherein $R^1$ represents alkyl having 2-6 carbon atoms;
$R^2$ represents methyl or ethyl;
$R^3$ represents alkyl having 1 to 5 carbon atoms;
W represents $(CH_2)_x$ where x is 2 to 7, alkylene having 2 to 7 carbon atoms, alkenylene having 3 to 7 carbon atoms, alkynylene having 3 to 7 carbon atoms, or cyclopentyl;
$R^4$ represents hydrogen, alkyl having 2-5 carbon atoms, alkenyl having 2 to 5 carbon atoms, or alkynyl having 2 to 5 carbon atoms;
Q represents oxygen or $CH_2$;
B represents $CH_2$, C=O or CH—OH;
$R^5$ represents hydrogen, alkyl having 1 to 6 carbon atoms, or $R^5$ and $R^6$ together optionally represent a carbon to carbon bond; or
$R^5$ represents alkanoyl having 2 to 4 carbon atoms, carboxy, alkoxycarbonyl, or $(CH_2)y$—$CO_2R^8$ wherein y is 0 to 4 and $R^8$ is hydrogen or alkyl having 1 to 6 carbon atoms; and
A represents —Z—$CO_2R^7$ or —Z—$COR^9 R^{10}$ wherein $R^7$ represents hydrogen or alkyl having 1 to 6 carbon atoms, $R^9$, $R^{10}$, represent hydrogen, alkyl having 1 to 6 carbon atoms, or cycloalkyl having 3 to 6 carbon atoms or $NR^9R^{10}$ form a heterocyclic ring, and wherein Z is absent or represents straight or branched chain alkylene or alkenylene having up to 6 carbon atoms.

These compounds are selective antagonists of leukotriene $B_4$(LTB$_4$) with little or no antagonism of leukotriene $D_4$ (LTD$_4$) and are useful anti-inflammatory agents for treating inflammatory bowel disease, rheumatoid arthritis, gout and psoriasis.

28 Claims, No Drawings

ALKOXY-SUBSTITUTED DIHYDROBENZOPYRAN-2-CARBOXYLATE DERIVATIVES

This is a continuation-in-part of United States Ser. No. 07/057,136 filed May 29, 1987, abandoned.

BACKGROUND OF THE INVENTION

1. Field Of The Invention

This invention is in the field of pharmaceutical agents which selectively act as leukotriene $B_4$ ($LTB_4$) antagonists.

2. Prior Art

The prior art discloses compounds having structures similar to Formula I except in the prior art compounds $R^2$ of Formula I is replaced with hydrogen. For example:

| | |
|---|---|
| EPA | 079,637 |
| EPA | 100,466.6 (U.S. Pat. No. 4,665,203) |
| U.S. Pat. No. | 4,595,882 |
| U.S. Pat. No. | 4,546,194 |
| EPA (U.S.S.N) 507383 | 129,906 |
| CA | 103 (19) 160 389 G |
| Japan | 60/42378 |
| EPA | 150447 |

*Journal of Medicinal Chemistry*, 1977, 20 (3) 376 broadly discloses compounds where $R^2$ of Formula I is hydrogen.

European Pat. No. 79,637 generically discloses a formula which encompasses compounds of Formula I wherein —$OR^2$ is —O-alkyl and B is C=O, but does not exemplify or otherwise enable the preparation and use of such compounds. European Pat. No. 79,637 extensively discloses intermediates to making compounds of this invention, that is, where —$OR^2$ in formula I is —OH. European Pat. No. 79,637 does not teach the selective $LTB_4$ antagonist activity of compounds of this invention.

U.S. Pat. No. 4,281,008, U.S. Pat. No. 3,822,148, and U.S. Pat. No. 4,006,245 generically disclose formulae which encompass compounds of Formula I wherein —$OR^2$ is —O-alkyl or O—Me and B is C=O but do not exemplify or otherwise enable the preparation and use of such compounds, nor do they teach the selective $LTB_4$ antagonist activity of compounds of the present invention.

*The Journal of Medicinal Chemistry*, 1977, Vol. 20 (3): 376 discloses a compound similar to the compounds of Formula I except the acyl and alkyl substituents adjacent the —$OR_2$ in Formula I are absent. *The Journal of Medicinal Chemistry* article also discloses a compound similar to compounds of Formula I except for a hydroxy substituent on the —O—$(CH_2)_x$—O— connecting group.

The prior art generally describes the above compounds as $LTD_4$ antagonists for use as anti-allergy compounds or as antagonists of SRS-A, the slow reacting substance of anaphylaxis. In sharp contrast compounds of Formula I are selective $LTB_4$ antagonists useful in treating inflammatory diseases.

Leukotriene $D_4$ and $C_4$ ($LTD_4$/$LTC_4$) and leukotriene $B_4$ ($LTB_4$) are products of the arachidonic acid metabolic pathway. $LTD_4$ and $LTC_4$ are associated with smooth muscle contraction and contract guinea pig ileum, human and guinea pig bronchi and human pulmonary artery and vein. $LTB_4$ is associated with neutrophil stimulation and is characterized by chemotaxis, aggregation and degranulation. $LTB_4$ is believed to be an important mediator of inflammation. High levels of $LTB_4$ are detected in rheumatoid arthritis, gout, psoriasis, and inflammatory bowel disease. Thus antagonists of $LTB_4$ are useful in the therapy of such diseases.

*Gastroenterology*, 1985: 88: 580–7 discusses the role of arachidonic acid metabolites in inflammatory bowel disease.

*British Medical Bulletin*, (1983), vol. 39, No. 3, pp. 249–254, generally discusses the pharmacology and pathophysiology of leukotriene $B_4$.

*Biochemical and Biophysical Research Communications*, Vol. 138, No. 2 (1986), pp. 540–546 discusses the pharmacology of a specific $LTB_4$ antagonist which has a different structure than compounds of this invention.

BRIEF DESCRIPTION OF THE INVENTION

This invention encompasses compounds of Formula I and the stereoisomers and pharmaceutically acceptable salts thereof;

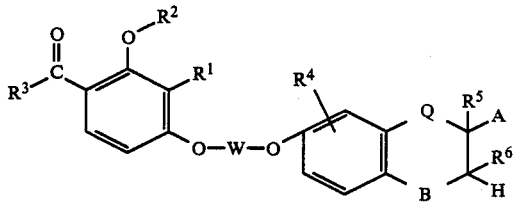

wherein
$R^1$ represents alkyl having 2–6 carbon atoms, alkenyl having 2 to 6 carbon atoms, alkynyl having 2 to 6 carbon atoms, or —$(CH_2)_n$—R wherein R represents cycloalkyl of 3 to 5 carbon atoms and n is 1 or 2;
$R^2$ represents methyl or ethyl;
$R^3$ represents alkyl having 1 to 5 carbon atoms;
W represents $(CH_2)_x$ where x is 2 to 7, alkenylene having 3 to 7 carbon atoms, alkynylene having 3 to 7 carbon atoms, or cyclopentyl;
$R^4$ represents hydrogen, alkyl having 2 to 5 carbon atoms, alkenyl having 2 to 5 carbon atoms, or alkynyl having 2 to 5 carbon atoms;
Q represents oxygen or $CH_2$;
B represents $CH_2$, C=O, or CH—OH;
$R^5$ represents hydrogen, alkyl having 1 to 6 carbon atoms, or $R^5$ and $R^6$ together optionally represent a carbon to carbon bond; or $R^5$ represents alkanoyl having 2 to 4 carbon atoms, carboxy, alkoxycarbonyl, or $(CH_2)y$—$CO_2R^8$ wherein y is 0 to 4 and $R^8$ is hydrogen or alkyl having 1 to 6 carbon atoms; and
A represents —Z—$CO_2R^7$ or —Z—$CONR^9R^{10}$ wherein $R^7$ represents hydrogen or alkyl having 1 to 6 carbon atoms, $R^9$ and $R^{10}$ represent hydrogen, alkyl having 1 to 6 carbon atoms, or cycloalkyl having 3 to 6 carbon atoms, or $NR^9R^{10}$ form a heterocyclic ring, and wherein Z is absent or represents straight or branched chain alkylene or alkenylene having up to 6 carbon atoms.

These compounds are selective antagonists of leukotriene $B_4$ ($LTB_4$) with little or no antagonism of leukotriene $D_4$ ($LTD_4$) and are useful anti-inflammatory agents for treating inflammatory bowel disease, rheumatoid arthritis, gout, and psoriasis.

DETAILED DESCRIPTION OF THE INVENTION

This invention encompasses the compounds of formula I as previously described.

Preferred embodiments of the present invention are compounds of the formula Ia, the stereoisomers and pharmaceutically acceptable salts thereof,

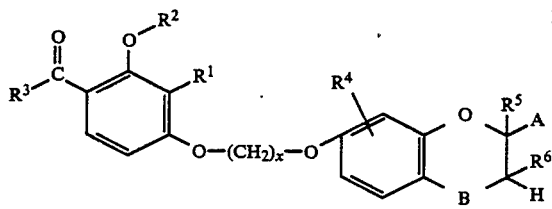

wherein
$R^1$ represents alkyl having 2–4 carbon atoms;
$R^2$ represents methyl or ethyl;
$R^3$ represents alkyl having 1 to 3 carbon atoms;
x represents 3 to 5;
$R^4$ represents alkyl having 2 to 4 carbon atoms;
B represents $CH_2$ or $C=O$;
$R^5$ represents hydrogen, alkyl having 1 to 4 carbon atoms, or $R^5$ and $R^6$ together optionally represent a carbon to carbon bond;
A represents $—Z—CO_2R^7$, wherein $R^7$ represents hydrogen or alkyl having 1 to 4 carbon atoms and wherein Z is absent or represents alkylene having up to 2 carbon atoms.

These compounds are selective antagonists of leukotriene $B_4$ ($LTB_4$) with little or no antagonism of leukotriene $D_4$ ($LTD_4$) and are useful anti-inflammatory agents for treating inflammatory bowel disease, rheumatoid arthritis, gout, and psoriasis.

More preferred embodiments are compounds of the formula II

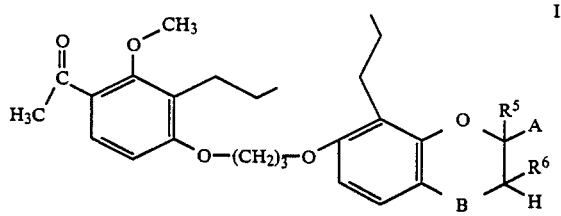

where $R_5$, A, B, $R^6$ are as previously defined in formula Ia.

Most preferred embodiments of the present invention are compounds of the formula IIa, the stereoisomers and pharmaceutcally acceptable salts thereof

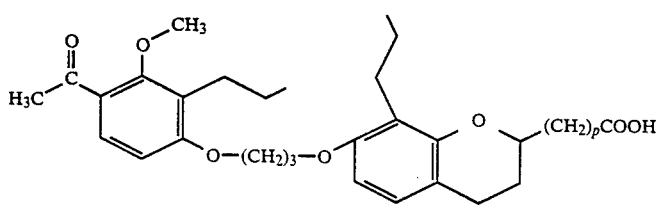

wherein p is 0 to 2.

A particularly preferred embodiment is the compound of the formula III:

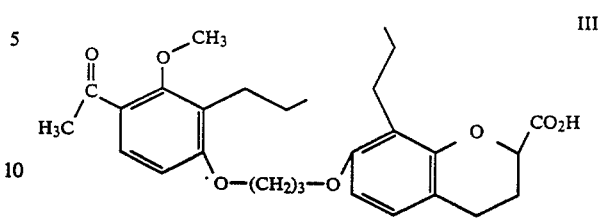

7-[3-(4-acetyl-3-methoxy-2-propylphenoxy)propoxy]-3,4-dihydro-8-propyl-2H-1-benzopyran-2-carboxylic acid and the pharmaceutically active salts thereof. This compound and its pharmaceutically acceptable salts are particularly preferred because of the specificity of the $LTB_4$ antagonist activity and its oral bioavailability.

Other compounds encompassed by this invention are as follows:

7-[3-(4-acetyl-3-methoxy-2-propylphenoxy)propoxy]-3,4-dihydro-4-oxo-8-propyl-2H-1-benzopyran-2-propanoic acid 7-[[5-(4-acetyl-3-methoxy-2-propylphenoxy)pentyl]oxy]-3,4-dihydro-8-propyl-2H-1-benzopyran-2-carboxylic acid, ethyl ester 7-[3-(4-acetyl-3-methoxy-2-propylphenoxy)propoxy]-3,4-dihydro-2-methyl-4-oxo-8-propyl-2H-1-benzopyran-2-propanoic acid 7-[3-(4-acetyl-3-methoxy-2-propylphenoxy)propoxy]-3,4-dihydro-8-propyl-2H-1-benzopyran-2-propanoic acid 7-[3-(4-acetyl-3-methoxy-2-propylphenoxy)propoxy]-2-carboxy-3,4-dihydro-4-oxo-8-propyl-2H-1-benzopyran-2-propanoic acid 7-[3-(4-acetyl-3-methoxy-2-propylphenoxy)propoxy]-3,4-dihydro-2-(methoxycarbonyl)-4-oxo-8-propyl-2H-1-benzopyran-2-propanoic acid, methyl ester 7-[3-(4-acetyl-3-methoxy-2-propylphenoxy)propoxy]-3,4-dihydro-2-methyl-8-propyl-2H-1-benzopyran-2-propanoic acid 7-[3-(4-acetyl-3-methoxy-2-propylphenoxy)propoxy]-3,4-dihydro-2-methyl-8-propyl-2H-1-benzopyran-2-propanoic acid, methyl ester 7-[3-(4-acetyl-3-methoxy-2-propylphenoxy)propoxy]-3,4-dihydro-2-methyl-4-oxo-8-propyl-2H-1-benzopyran-2-propanoic acid 7-[3-(4-acetyl-3-methoxy-2-propylphenoxy)propoxy]-3,4-dihydro-2-methyl-4-oxo-8-propyl-2H-1-benzopyran-2-propanoic acid, methyl ester 7-[3-[4-acetyl-2-(cyclopropylmethyl)-3-methoxyphenoxy]propoxy]-3,4dihydro-8-propyl-2H-1-benzopyran-2-carboxylic acid Alkyl defined for $R^1$, $R^2$, $R^3$, $R^4$, $R^5$, $R^6$, $R^7$, $R^8$, $R^9$ and $R^{10}$ is straight or branched chain alkyl having the indicated number of carbon atoms.

Pharmaceutically acceptable salts such as ammonium, sodium, potassium, alkaline earth, tetraalkylammonium and the like are encompassed by the invention.

Compounds of this invention are generally prepared by alkylating the prior art phenol hydroxy ($R^2$=H) compounds to form compounds of formula I by conventional techniques. Thus, the reaction of the phenol hydroxy ($R^2$=H) with methyl iodide in potassium carbonate provides the ether. Dimethyl sulfate in acetone and base is also useful in preparing ethers. Alternatively intermediates can be alkylated prior to forming the —O—(CH$_2$)—O— bridge. Hydrolysis of the ester compounds in the presence of lithium hydroxide and methanol gives the acid compounds.

The biological activity of compounds of this invention is indicated by the following tests.

PREPARATION OF HUMAN NEUTROPHILS

Neutrophils were purified from venous blood of normal human donors using standard techniques of dextran sedimentation, centrifugation on Ficoll-paque ® (Pharmacia) or Histopaque ® sterile solution (Sigma) and hypotonic lysis of erythrocytes (Boyum, A., *Isolation of Leukocytes From Human Blood: Further Observations. Scand. J. Lab. Clin. Invest.*, 21 (Suppl. 97): 31, 1968). The purity of isolated neutrophils was >95%.

LTB$_4$ RECEPTOR BINDING ASSAY

Neutrophils (4–6×10$^6$) in 1 ml Hanks' balanced salt solution containing 10 mM HEPES buffer (HBSS), pH 7.4 and 30 μM nordihydroguaiaretic acid were incubated with 0.6×10$^{-9}$M ($^3$H) LTB$_4$ in the presence or absence of test compounds. The incubation was carried out at 0° C. for 45 minutes and terminated by adding 5 ml of ice-cold HBSS followed by rapid filtration of incubation mixture under vacuum through GF/C glass fiber filters. The filters were further washed with 10 ml HBSS and radioactivity was determined. Specific binding was defined as the difference between total binding and nonspecific binding which was not displaced by 10$^{-7}$M unlabeled LTB$_4$. All data refer to specific binding.

HUMAN NEUTROPHIL DEGRANULATION ASSAY

Neutrophil degranulation was determined by measuring the release of myeloperoxidase activity into the incubation medium. Neutrophils (3×10$^6$) in 1 ml HBSS solution were preincubated with cytochalasin B (5 μg) at 37° C. for 5 minutes, followed by preincubation with test compounds for 7 minutes. Neutrophils were then incubated for 2 to 20 minutes with either LTB$_4$ (5×10$^{-8}$M) or the chemotactic peptide f-met-leu-phe (5×10$^{-6}$M) to induce degranulation. Following incubation, samples were centrifuged and myeloperoxidase was extracted from the cell pellets by sonication in phosphate buffer containing 0.4% Triton X-100. Triton X-100 was also added to the supernatants to a concentration of 0.4%. The supernatants and the pellet - extracts were then assayed spectrophotometrically for myeloperoxidase activity by determining the rate of decomposition of H$_2$O$_2$ with o-dianisidine as hydrogen donor as described by Renlund, et al. (Renlund, D. G., MacFarlane, J. L., Christensen, R. D., Lynch, R. E., and Rothstein, G., *A Quantitative And Sensitive Method For Measurement Of Myeloperoxidase*, Clinical Research 28:75A, 1980). Myeloperoxidase activity released into the supernatant was expressed as the percent of the average total activity (pellet plus supernatant).

GUINEA PIG LTB$_4$-INDUCED DERMAL CHEMOTAXIS

Test compound was administered intravenously or intragastrically at various times prior to the injection of leukotriene B$_4$ (LTB$_4$). LTB$_4$ was diluted in phosphate buffered saline (PBS) and 35 ng in 0.2 ml were injected intradermally into the shaven backs of anesthetized guinea pigs. PBS was injected as control. Four hours later, animals were sacrificed, skins removed and stored frozen (−70° C.). Injection sites were removed with a skin punch and mechanically homogenized (Polytron, Brinkmann Instruments). Myeloperoxidase (MPO), a marker enzyme for neutrophils, was extracted with 0.5% hexadecyltrimethylammonium bromide in 50 mM potassium phosphate buffer (pH 6.0), using sonication and freeze-thaw procedures. After centrifugation (40,000× g, 30 minutes), enzyme activities in the supernatants were assayed spectrophotometrically (A$_{460}$) by measuring the decomposition of hydrogen peroxide with o-dianisidine after 15 minutes. MPO activity was found to be proportional to the number of neutrophils. In guinea pigs the level of MPO activity increased with the amount of LTB$_4$ injected.

MODIFIED BOYDEN CHAMBER CHEMOTAXIS

Human neutrophils were isolated from citrated peripheral blood using standard techniques of dextran sedimentation, followed by centrifugation on Histopaque ® sterile solution (Sigma) or Ficoll-paque ® (Pharmacia) and hypotonic lysis of erythrocytes. A final cell suspension of 3.4×10$^6$ neutrophils/ml of HEPES-buffered Hanks balanced salt solution (HBSS, pH 7.3) was added to the upper well (0.8 ml) of a modified Boyden chamber (blind well). The lower well (0.2 ml), separated by a polycarbonate membrane (Nuleopore Corp.), contained HBSS or 3×10$^{-8}$M LTB$_4$ in the presence of absence of test compound. Following a 90 minute incubation at 37° C. in 5% CO$_2$-95% air, cells from the lower well were lysed and nuclei counted in a Model S-Plus-IV Coulter Counter. Percent inhibition was calculated from cell counts corrected for random migration by subtracting the mean of the HBSS control.

The compounds of this invention can be administered in a number of dosage forms. A preferred method of delivery would be oral or in such a manner so as to localize the action of the inhibitor. In an inflammatory condition such as rheumatoid arthritis the compounds could be injected directly into the affected joint. The compounds could also be administered in oral unit dosage forms such as tablets, capsules, pills, powders or granules. They may be introduced intraperitoneally, subcutaneously, or intramuscularly using forms known to the pharmaceutical art. Topical application in the form of salves and ointments are useful for treating psoriasis. Regardless of the route of administration selected, the compounds are formulated into pharmaceutically acceptable dosage forms by conventional methods known to the pharmaceutical art.

LTD$_4$ ANTAGONISM IN GUINEA PIG ILEUM

Fresh segments of guinea pig ileum were suspended in 2 ml. tissue baths containing oxygenated modified Tyrodes solution. After an equilibration period, an agonist dose-response curve was generated by exposing each tissue to 4 different $LTD_4$ doses and measuring the ensuing contractile heights. The ileum segments were washed and rested between exposures to agonist. Following this, the tissues were incubated with a single concentration of test compound and the agonist dose-response procedure was repeated. The dose ration is a measure of the antagonist's ability to shift the agonist dose-response curve to the right. It is derived as the concentration of agonist necessary to reach a given response level in the present (A') versus the absence (A) of antagonist. For example, if the test concentration of compound had no effect on the agonist-induced response (A'=A) the dose-ratio would approximate 1. Dose-ratios increase if the compound inhibits the agonist-induced response. One dose-ratio value is determined for each strip of ileum used to test antagonist. If the dose-ratios increase as a function of increasing antagonist concentration, these data may be evaluated by Schild analysis to determine whether the inhibition is competitive and if so, what the $pA_2$ value is for the compound. Schild analysis examines the linearity of the function described by the dose-ratios written as log (A'/A) versus antagonist concentration. If linearity is confirmed and the slope approximates −1, inhibition is considered to be competitive. The $pA_2$ is the negative log of the antagonist concentration required to produce a dose-ratio of 2. This value is considered to be a measure of the affinity of the competitive antagonist.

LEUKOTRIENE $D_4$ RECEPTOR ASSAY USING GUINEA PIG LUNG PREPARATIONS

The following description discloses an LTD4 radioreceptor assay used to identify compounds which inhibit LTD4 binding to lung membrane preparations.

MEMBRANE PREPARATIONS: For each membrane preparation, 10-11 male Hartley guinea pigs, weighing less than 350 gm, were sacrificed by guillotine. The lungs were rapidly removed and placed in ice-cold 50 mM Trisma 7.0 buffer. After all the lungs were collected, each was probed free of bronchial tissue to at least the level of tertiary branching as observed through a dissecting lamp. The tissue was minced with a razor blade on a damp paper towel and placed into fresh ice-cold Trisma 7.0 buffer. When all the tissues had been processed, they were pooled, drained and weighed. Nine volumes of cold buffer were added and the tissue was polytroned for 6-10 second bursts with a 1 minute cool down period in an ice bath between each burst. The homogenate was filtered through a gauze pad and centrifuged at 1085× g for 15 minutes at 4° C. Supernatants were saved and centrifuged at 40,000× g for 20 minutes at 4° C. This time, supernatants were discarded and the pellets were resuspended in 30-35 ml fresh Trisma 7.0 buffer by 1-10 second bursts with the polytron. The materials were centrifuged again at 40,000× g. Supernatants were again discarded. Each pellet was resuspended again with approximately 7 ml buffer. All this material was pooled into a 100 ml polypropylene container and stirred with a magnetic stirring bar. The tubes were rinsed with small amounts of buffer and the rinse was added to the membrane preparation. The homogenized membranes were aliquoted into 1.5 ml microfuge tubes and frozen at −70° C. Three aliquots were submitted for protein determinations by FPB (fluorescamine protein binding) assay. This procedure usually resulted in protein concentrations ranging from 1-5 mg/ml.

RADIORECEPTOR ASSAY METHODS: Each guinea pig lung preparation yielded enough protein to last through several months of assaying. Because of this, each preparation was tested for its $3H-LTD_4$ dissociation constant, number of receptor populations, number of binding sites per unit protein, and the dose-response displacment characteristics by $LTD_4$ and the receptor antagonist FPL 55712.

Unless otherwise indicated, all binding experiments were performed in a final incubation volume of 250 μl. Tritiated $LTD_4$ was obtained from New England Nuclear and nonradioactive $LTD_4$ was purchased from Biomol Research Laboratories, Inc. (Philadelphia, PA). Both materials were received in solutions. $3H-LTD_4$ was solubilized in 50% EtOH with 0.01M pH 6.8 phosphate buffer while Biomol $LTD_4$ was prepared in 65% MeOH with 35% water and small amounts of AcOH and $NH_4OH$. Both solutions were brought to appropriate assay concentrations by dilution in assay buffer consisting of 50 mM Trisma 7.4 with 5 mM L-cysteine and 20 mM $CaCl_2$. Membranes were also diluted with this assay buffer. Compounds other than $LTD_4$ were solubilized in DMSO and added to each tube in 5 μl aliquots. Diluent was added to all other appropriate control tubes. Incubations were conducted for 30 minutes at 25° C. in a shaking water bath. Termination of the reaction was achieved by pouring the incubate over 2.5 cm Whatman GF/C filters soaked in assay buffer and set over the ports of Millipore filter vacuum manifolds. Filters were rinsed with 4 ml ice cold assay buffer 3 times. The filters were removed, placed in 10 ml Aquasol scintillation cocktail and allowed to cool in the dark for 2 hours prior to counting. All samples were corrected for background and isotope decay before converting DPM determination to mass.

DETERMINATION OF $IC_{50}$ VALUES: $LTD_4$ specific binding was determined as the difference between $3H-LTD_4$ binding alone and in the presence of 1 mM unlabeled $LTD_4$. Nonspecific $LTD_4$ binding was also removed from tubes containing compound as well. The percent inhibition of binding for each dose of compound was calculated by subtracting specific binding in the presence of compound from $LTD_4$ specific binding in the absence of compound. This result was then divided by the specific binding without compound and multiplied by 100. These values were logit-transformed and linear regression was performed on the dose-response data. All dose-response sets used to calculate $IC_{50}$ values contained data from 3-6 compound concentrations. Correlation coefficients for the straight line model almost always exceeded 0.98. $IC_{50}$ values were calculated from the regression equation for the line.

The compounds of the present invention are formulated into pharmaceutically acceptable dosage forms by conventional methods known to those skilled in the art. The compounds may be administered in a number of dosage forms, for example, such oral dosage forms as tablets, capsules, pills, powders, or granules. They may also be administered intravascularly, intraperitoneally, subcutaneously, or intramuscularly using forms known to the pharmaceutical art.

An effective but non-toxic quantity of the compound is employed in treatment. The dosage regimen for inhibition of $LTB_4$ by the compounds of this invention is selected in accordance with a variety of factors including the type, age, weight, sex, and medical condition of the mammal, the particular disease and its severity, the route of administration and the particular compound employed. An ordinarily skilled physician or veterinarian will readily determine and prescribe the effective amount of the compound to prevent or arrest the progress of the condition. In so proceeding, the physician or veterinarian could employ or use relatively low dosages at first, subsequently increasing the dose until a maximum response is obtained. A dosage range of 1 to 25 mg/kg generally provides a therapeutically effective anti-inflammatory response.

The following examples illustrate the preparation of compounds of this invention from known starting materials. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted.

U.S. Pat. No. 4,665,203 issued May 12, 1987 discloses methods for making some of the intermediates used in making compounds of the present invention.

EXAMPLE 1

7-[3-(4-acetyl-3-methoxy-2-propylphenoxy)propoxy]-3,4-dihydro-8-propyl-2H-1-benzopyran-2-carboxylic acid.

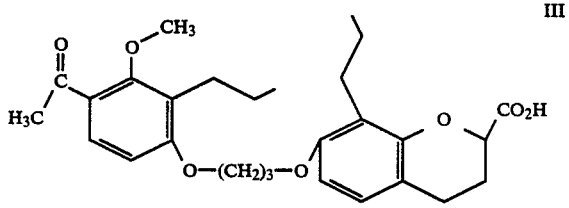

III (a) 493 mg of methyl 7-[3-(4-acetyl-3-hydroxy-2-propylphenoxy)propoxy]-3,4-dihydro-8-propyl-2H-1-benzopyran-2-carboxylate was added to 25 ml of acetone containing 276 mg of anhydrous potassium carbonate and 282 mg of methyl iodide. The mixture was refluxed for about 24 hours and water was added and the mixture was then extracted with ethyl acetate. The extract was dried, the solvent removed under vacuum, and the residual oil was chromatographed over silica gel with a 40/60 mixture of ethyl acetate/hexane to provide pure methyl ether, methyl 7-[3-(4-acetyl-3-methoxy-2-propylphenoxy)propoxy]-3,4-dihydro-8-propyl-2H-1-benzopyran-2-carboxylate having the formula

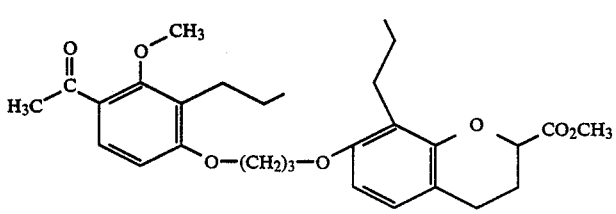

1a (b) The methyl ether (1a) (340 mg) was dissolved in methanol (5 ml) containing lithium hydroxide (0.7 ml of a 2N LiOH solution in water). The mixture was stirred at room temperature overnight and the solvent re-moved in vacuo. The residue was partitioned between ethyl acetate and 2N HCl and the organic layer separated and washed with brine. Evaporation of the volatiles in vacuo afforded crude acid of Formula III. This material was purified by silica gel chromatography using ethyl acetate/hexane/acetic acid (40:60:0.5) as eluant. The pure product was recrystallized from ethyl acetate/hexane to afford 200 mg of product, 7-[3-(4-acetyl-3-methoxy-2-propylphenoxy)propoxy]-3,4-dihydro-8-propyl-2H-1-benzopyran-2-carboxylic acid, m.p. 65°–68° C.

Microanalysis: Found: C 69.22, H 7.53. Theory: C 69.40, H 7.49.

The NMR (CDCl$_3$) shows a —OCH$_3$ at $\delta 3.75$.

EXAMPLE 2

Comparative Test Data For Compound III

|  | LTB$_4$ Receptor Binding | Guinea Pig Ileum Contraction pA$_2$ |
|---|---|---|
| Compound III | 50% at 0.3 μM | 6.5 or less |
| Compound III where —OCH$_3$ is replaced with —OH | 30% at 1 μM | 7.6 |

| | Guinea Pig Ileum Results | |
|---|---|---|
| Compound | Test Concentration (M) | Dose Ratio |
| Compound III where —OCH$_3$ is replaced with —OH | $1 \times 10^{-6}$ | 100 |
|  | $3 \times 10^{-7}$ | 13.24 |
|  |  | 9.97 |
|  |  | 17.04 |
|  |  | 10.59 |
|  | $1 \times 10^{-7}$ | 3.48 |
|  |  | 7.38 |
|  | $3 \times 10^{-8}$ | 1.71 |
|  |  | 1.97 |
|  |  | 3.10 |
|  |  | 1.89 |
| Compound III | $3 \times 10^{-6}$ | 8.65 |
|  |  | 11.16 |
|  | $1 \times 10^{-6}$ | 2.54 |
|  |  | 1.95 |
|  | $3 \times 10^{-7}$ | 2.28 |
|  |  | 1.67 |

Thus, the —OCH$_3$ compound (III) is about 5× more potent than the —OH compound in LTB$_4$ receptor binding and at least 10× less active as an LTD$_4$ antagonist in the guinea pig ileum smooth muscle contraction test. Compounds of this invention are selective LTB$_4$ antagonists useful in treating inflammatory disease.

EXAMPLE 3

7-[3-[4-acetyl-2-(cyclopropylmethyl)-3-methoxyphenoxy]propoxy]-3,4-dihydro-8-propyl-2H-1-benzopyran-2-carboxylic acid.

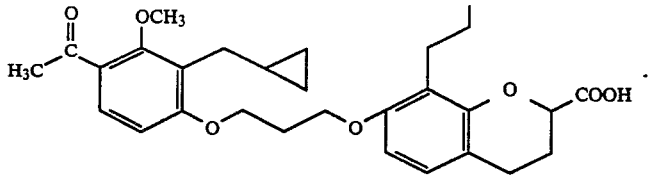

(a) A mixture of Zinc/copper couple (509 mg, 7.8 mMol), iodine (2 mg), and methylene iodide (2.09 g, 7.8 mMol) was suspended in ether (5 ml) and the mixture heated to reflux for 30 minutes. The heat was removed and 2,4-dihydroxy-3-allylacetophenone (500 mg, 2.6 mMol) was added as a solution in ether. The mixture was heated at reflux for 2 hours and a further 2 g of methylene iodide was added during this time. The mixture was cooled and stirred at room temperature for 10 hours. The mixture was filtered and the ether solution washed sequentially with aqueous ammonium chloride, sodium bicarbonate and brine. The organic layer was dried over sodium sulfate and evaporated in vacuo to afford a crude residue which was purified by column chromotography on silica gel (eluting with 2:8 ethyl acetate/hexane to give 220 mg of 2,4-dihydroxy-3-cyclopropylmethylacetophenone NMR $^1$H ($\delta$,CDCl$_3$) 0.25-0.5 (4H, m, cyclopropyl H's), 1.0 (1H, m, cyclopropyl H), 2.5 (3H, s, acetyl CH$_3$, 2.65(2H,d,CH$_2$-$\phi$) 6.4(1H,d,ArH), 7.5(1H,d,ArH).

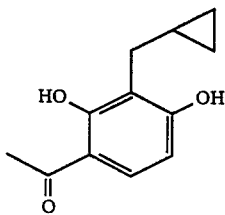

(b) 1,3 chlorobromopropane (1.9 g), methyl 7-hydroxy-8-propylchroman-2-carboxylate (2.5 g) and potassium carbonate (2.1 g) were stirred at RT in dry dimethylformamide under argon for 24 hours. The mixture was poured into water and thoroughly extracted with ethyl acetate. The combined organic extracts were washed sequentially with water and brine and then dried over magnesium sulfate. Filtration and evaporation of the volatiles in vacuo afforded 4.3 g of crude product which was chromotographed on silica gel (10:90 ethyl acetate/hexane) to provide 3.0 g of methyl 7-(3-chloropropoxy)-8-propylchroman-2-carboxylate.

NMR $^1$H ($\delta$, CDCl$_3$), 0.8(3H,t, propyl CH$_3$) 1.5-2.6 (8H,m propyl CH$_2$'s and ring CH$_2$'s), 3.7 (3H,s,CO$_2$CH$_3$), 3.75 (2H,t,CH$_2$Cl), 4.2 (2H,t, CH$_2$OAc), 4.75(1H,d,CH—OAr) 6.4 (1H,d, ArH), 6.8 (1H,d,ArH).

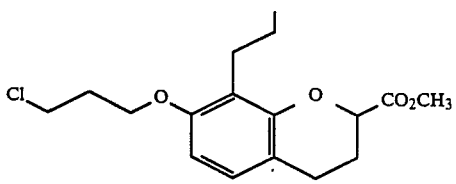

(c) 2,4-dihydroxy-3-cyclopropylmethylacetophenone (0.2 g), methyl 7-(3-chloropropoxy)-8-propylchroman-2-carboxylate (327 mgs), sodium iodide (0.15 g) and potassium carbonate (0.14 g) were stirred in 3 ml dry dimethylformamide (DMF) overnight at 45° under argon. The mixture was poured into water and thoroughly extracted with ethyl acetate. The combined organic extracts were washed with water and dried over magnesium sulfate. Evaporation of the volatiles in vacuo afforded a crude oil which was purified by chromatography on silca gel to give 98 mgs of methyl 7-[3-[4-acetyl-2-(cyclopropylmethyl)-3-hydroxyphenoxy]propoxy]-3,4-dihydro-8-propyl-2H-1-benzopyran-2-carboxylate.

NMR: $^1$H($\delta$,CDCl$_3$) 0.2-0.45 (4H, m, cyclopropyl H's), 0.9 (3H, t, propyl CH$_3$), 1.0(1H, m, cyclopropyl H), 1.4-2.8(12H, m, aliphatic and cyclic CH$_2$'s), 2.55 (3H, s, CH$_3$CO), 3.75 (3H, s, CO$_2$CH$_3$), 4.25 (2H, t, CH$_2$OAr), 4.35(2H,t,CH$_2$OAr), 4.75(1H,m, CH—OAr), 6.4-7.6(4H,m,ArH's).

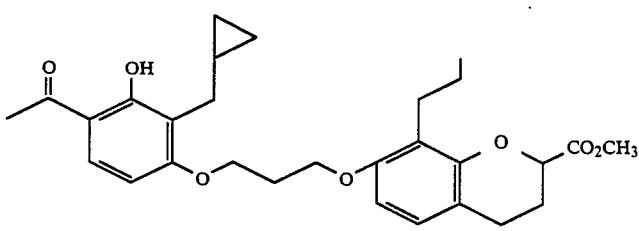

(d) Compound 3c (95 mg) was dissolved in acetone (5 ml) containing dimethyl sulfate (38 mg) and potassium hydroxide (12.4 mg) and the mixture was heated at 56° C. under argon for 10 hours. The solvent was removed in vacuo and the residue partitioned between ethyl acetate and water. The organic layer was separated, washed with potassium carbonate solution and dried over magnesium sulfate. Evaporation of the volatiles in vacuo afforded a crude oil which was purified by chromatography on silica gel (1:9 ethyl acetate/hexane) to give 40 mg of pure methyl 7-[3-[4-acetyl-2-(cyclo-propylmethyl)-3-methoxyphenoxy]propoxy]-3,4-dihydro-8-propyl-2H-1-benzopyran-2-carboxylate.

NMR $^1$H($\delta$,CDCl$_3$) 3.5(3H,s,OCH$_3$).

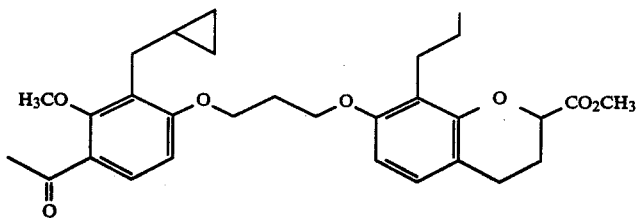

3d (e) Compound 3d (38 mg), was dissolved in 0.3 ml of methanol containing 74 μl of a 1M lithium hydroxide solution, and the solution was stirred overnight at room temperature. The solvent was removed and the residue partitioned between ethyl acetate and 10% hydrochloric acid solution. The organic layer was removed and dried over magnesium sulfate. Evaporation of the volatiles in vacuo afforded 35 mg of the title compound, 7-[3-[4-acetyl-2-(cyclopropylmethyl)-3-methoxyphenoxy]propoxy]-3,4-dihydro-8-propyl-2H-1-benzopyran-2-carboxylic acid.

Microanalysis: Found C 69.51, H 7.34. Calculated for C$_{29}$H$_{36}$O$_7$.¼H$_2$O: C 69.30, H 7.49.

EXAMPLE 4

7-[[3-(4-acetyl-3-methoxy-2-propylphenoxy)cyclopentyl]oxy]-3,4-dihydro-8-propyl-2H-1-benzopyran-2-carboxylic acid.

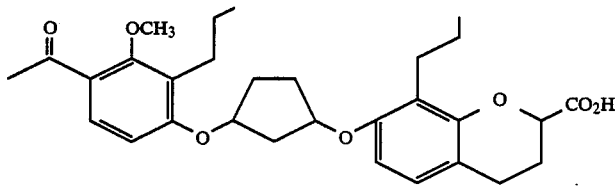

(a) 2,4-dihydroxy-3-propyl acetophenone (1.94 g), 1,3-dihydroxycyclopentane (1.02 g), triphenylphosphine (2.62 g), and diethyl azodicarboxylate (1.7 g) were dissolved in dry tetrahydrofuran (THF) (200 ml) and stirred under argon at room temperature overnight. The solvent was evaporated and the crude residue purified by silica gel chromatography (Merck 60, 4:6 ethyl acetate/hexane) to afford 1.5 g of 1-(2-propyl-3-hydroxy-4-acetylphenoxy)-3-hydroxycyclopentane.

NMR $^1$H ($\delta$, CDCl$_3$) 0.9 (3H,t,propyl CH$_3$), 1.3-2.6(10H, aliphatic and cyclic CH$_2$'s), 2.55 (3H,s, CH$_3$CO), 4.4 (1H, m, CH—OH), 4.9 (1H, m, CH—OAr), 6.4 (1H, d, ArH), 7.6 (1H, d, ArH).

(b) Compound 4a (1.4 mg, 5.0 mMol), methyl 7-hydroxy-8-propylchroman-2-carboxylate (1.33 mg, 5.01 mMol), triphenylphosphine (1.32 mg, 5.0 mMol) and diethyl azodicarboxylate (875 mg) were dissolved in dry tetrahydrofuran (120 ml) and stirred under argon at room temperature for 10 hours. The solvent was evaporated and the solid residue dissolved in dry ether and filtered through sintered glass. The filtrate was evaporated and the residue purified by chromatography on silica gel using 2:8 ethyl acetate/hexane as eluant. 0.7 g of methyl 7-[[3-(4-acetyl-3-hydroxy-2-propylphenoxy)-cyclopentyl]oxy]-3,4-dihydro-8-propyl-2H-1-benzopyran-2-carboxylate were obtained.

NMR $^1$H($\delta$, CDCl$_3$) 0.9(6H,t, propyl CH$_3$'s), 1.5-2.7 (18H, aliphatic and cyclic CH$_2$'s), 2.55(3H,s,CH$_3$CO), 3.75 (3H,s, OCH$_3$), 4.75(1H,m,C$\underline{H}$—CO$_2$CH$_3$), 4.9(1H,m,CH—OAr), 5.0(1H, m,C$\underline{H}$—OAr), 6.4 (2H,2ds, ArH's) 6.8(1H,d,ArH), 7.55(1H,d,ArH).

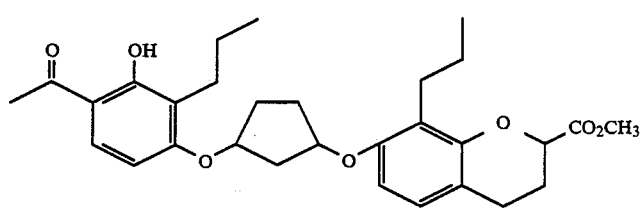

4b (c) Compound 4b (419 mg, 0.8 mMol) was dissolved in acetone (10 ml) containing potassium hydroxide (55.3 mg, 0.98 mMol), and dimethyl sulfate (134,5 mg). The mixture was heated at 45° C. for 10 hours and then cooled and the volatiles removed in vacuo. The residue was partitioned between ethyl acetate and water and the organic layer separated and dried over magnesium sulfate. Removal of solvent afforded a crude oil which was purified using radial band chromatography (Harrison chromatotron, 2:8 ethyl acetate/hexane as eluant).

Methyl 7-[[3-(4-acetyl-3-methoxy-2-propylphenoxy)cyclopentyl]oxy]-3,4-dihydro-8-propyl-2H-1-benzopyran-2-carboxylate was obtained pure as a colorless oil (270 mg).

NMR ¹H(δ,CDCl₃) 0.9(6H, 2t's, propyl CH₃'s), 1.5–2.8 (18H, aliphatic and cyclic CH₂'s), 2.6 (3H, s, CH₃CO), 3.75 (3H, s, OCH₃ ether), 3.77 (3H,s,OCH₃ ester), 4.75 (1H,m, CHCO₂CH₃), 4.9 (1H,m, CH—OAr), 5.0 (1H,m CH—OAr), 6.4(1H,d, ArH), 6.65 (1H,d, ArH), 6.8(1H,d,ArH), 7.55 (1H,d,ArH).

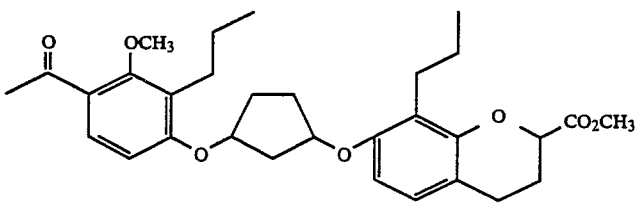

4c (d) Compound 4c (150 mg) was dissolved in methanol (2 ml) containing 1M lithium hydroxide (450 μL) and the mixture was stirred at room temperature overnight. The volatiles were removed in vacuo and the residue partitioned between ethyl acetate and dilute hydrochloric acid. The organic layer was separated and dried over magnesium sulfate. Removal of solvent afforded the title compound, 7-[[3-(4-acetyl-3-methoxy-2-propylphenoxy)cyclopentyl]oxy]-3,4-dihydro-3-propyl-2H-1-benzopyran-2-carboxylic acid.

NMR ¹H(δ, CDCl₃) no OCH₃ ester at 3.77.

EXAMPLE 5

7-[3-[4-acetyl-3-methoxy-2-(2-propenyl)phenoxy]propoxy]-3,4-dihydro-8-propyl-2H-1-benzopyran-2-carboxylic acid.

potassium carbonate (26.91 g, 195 mMol). The mixture was allowed to stir at room temperature under nitrogen for 8 hours and then partitioned between water and toluene. The organic layer was separated and washed with water and brine and then dried over sodium sulfate. Evaporation of the volatiles in vacuo afforded 36 g of crude product which was chromatographed on Merck 60 silica gel using 5:95 ethyl acetate/toluene as eluant. 25 g of pure methyl 7-[3-[4-acetyl-3-hydroxy-2-(2-propenyl)phenoxy]propoxy]-3,4-dihydro-8-propyl-2H-1-benzopyran-2-carboxylate were obtained in this manner.

NMR ¹H (δ, CDCl₃) 0.9(3H,t,propyl CH₃), 1.4–2.8(OH, aliphatic and cyclic CH₂'s), 2.55 (3H,d, CH₃CO), 3.45(2H,d,ArCH₂CH=CH₂), 3.75 (3H,s,CO₂CH₃), 4.09(2H,t, CH₂OAr), 4.22(2H,t,CH₂OAr) 4.75(1H,t,CHOAr); 4.85–5.00(2H,m,allyl H's), 5.75–6.1(1H,m,allyl CH) 6.4–7.12(4H,ArH's).

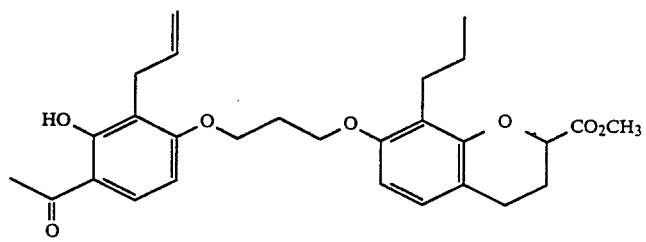

5a (b) Compound 5a (20.6 g, 42.7 mMol) was dissolved in dry DMF (105 ml) containing methyl iodide (18.4 g, 128.5 mMol) and powdered potassium carbonate (17.69 g, 128 mMol). The mixture was stirred under nitrogen at room temperature for 22 hours and then partitioned between water and toluene. The organic layer was separated, washed with water and brine and dried over sodium sulfate. Removal of the volatiles in vacuo af-

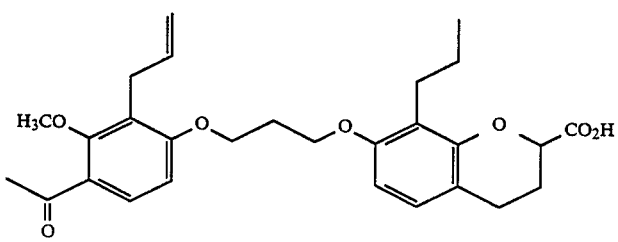

(a) 2,4-Dihydroxy-3-(2-propenyl) acetophenone (Aldrich, 12.5 g, 65 mMol) and methyl 7-(3-iodopropoxy)-8-propylchroman-2-carboxylate (29.9 g, 71.5 mMol) were dissolved in DMF (300 ml) containing powdered forded 21 g of product which was methyl 7-[3-[4-acetyl-3-methoxy-2-(2-propenyl)phenoxy]propoxy]-3,4-dihydro-8-propyl-2H-1-benzopyran-2-carboxylate.

NMR ¹H(δ,CDCl₃) 3.77 (3H, s, OCH₃ ether).

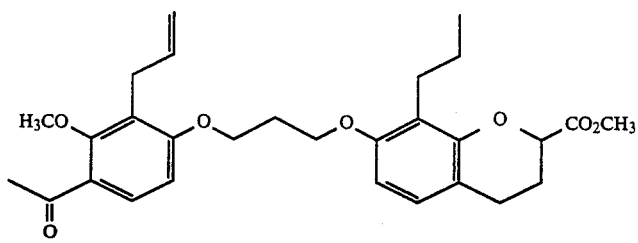

5b (c) Compound 5b (16.96 g, 34.15 mMol) was dissolved in methanol and a solution of lithium hydroxide in water (4.3 g in 43 ml 102.5 mMol) was added. The mixture was stirred at room temperature for 3 hours and the solvent removed in vacuo. The mixture was partitioned between toluene and dilute hydrochloric acid and the organic layer removed. The organic extract was washed sequentially with water, brine and then dried over sodium sulfate. Evaporation of the volatiles in vacuo afforded a yellow oil which was purified by silica gel chromatography on Biosil A using 20% ethyl acetate in toluene as eluant. The product, 7-[3-[4-acetyl-3-methoxy-2-(2-propenyl)phenoxy]propoxy]-3,4-dihydro-2H-1-benzopyran-2-carboxylic acid was isolated as a light yellow oil, 15 g, which was recrystallized from ethyl acetate/hexane, mp 85.5° C.

Microanalysis: Found, C 69.69, H 7.10. Calculated for $C_{28}H_{35}O_7$, C 69.6, H 6.98.

EXAMPLE 6

7-[3-(4-acetyl-3-methoxy-2-propylphenoxy)propoxy]-3,4-dihydro-2H-1-benzopyran-2-carboxylic acid

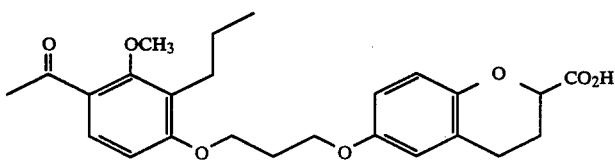

(a) 2,4-dihydroxyacetophenone (7.1 g, 0.05 mol) and dimethyl oxylate (7.2 g) were dissolved in DMF containing a solution of sodium methoxide in methanol (4.0 g Na, 100 ml MeOH) and the mixture was stirred at room temperature for 48 hours. At this point, acetic acid (180 ml) was added and the mixture was heated to 100° C. for 5 hours. The solvent was removed in vacuo and the residue partitioned between ethyl acetate and water. The organic layer was separated, the aqueous layer was thoroughly extracted with more ethyl acetate, and the combined organic extracts were washed with brine. Evaporation of the dried ($Na_2SO_4$) solvent in vacuo afforded methyl 7-hydroxy-4-oxo-4H-1-benzopyran-2-carboxylate (6a) as a crude yellow solid which was crystallized from from ethyl acetate/hexane to afford 3.5 g of pure product.

NMR $^1H$ ($\delta$, $CDCl_3$) 4.0 (3H, s, $CO_2CH_3$), 6.85 (1H, s, chromenone H) 6.9–8.0 (3H, Ar H's).

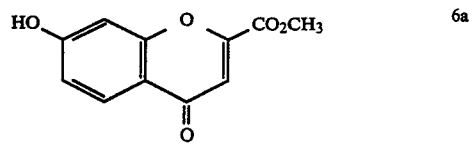

6a (b) Compound 6a (3.57 g, 16 mMol) was dissolved in ethyl acetate containing phosphoric acid and 5% palladium on carbon. The mixture was shaken in a Parr apparatus at room temperature under an atmosphere of hydrogen for 22 hours. The solution was filtered and washed with water and the organic layer was dried over magnesium sulfate. Evaporation of the volatiles in vacuo afforded a crude oil which was purified by silica gel chromatography using ethyl acetate/hexane 6:4 as eluant. 3.3 g of product, methyl 7-hydroxy-chroman-2-carboxylate, (6b) was obtained as a clear oil.

NMR: $^1H$ ($\delta$, $CDCl_3$) 2.1–2.8 (4H, m, cyclic $CH_2$'s 3.8(3H,s, $CO_2CH_3$), 4.7 (1H, dd, CHOAr), 6.35–6.9(3H, Ar H's).

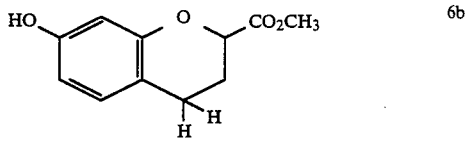

6b (c) Compound 6b (416 mg, 2 mMol) and 3-(2-propyl-3-hydroxy-4-acetylphenoxy)-1-iodopropane (720 mg, 2 mMol) were dissolved in dry DMF (3 ml) containing powdered anhydrous potassium carbonate (552 mg, 4 mMol) and the mixture was stirred at 60° C. for 10 hours. The mixture was cooled and partitioned between ethyl acetate and water. The organic layer was separated, washed with water and dried over magnesium sulfate. Evaporation of the volatiles in vacuo afforded a crude oil which was purified by flash chromatography on Merck 60 silica gel using ethyl acetate and hexane (2.5:7.5) as eluant. 540 mg of product, methyl 7-[3-(4-acetyl-3-hydroxy-2-propylphenoxy)propoxy]3,4-dihydro-8-propyl-2H-1-benzopyran-2-carboxylate, (6c) were obtained.

NMR: $^1H$($\delta$, $CDCl_3$) 0.9 (3H, t, propyl H's), 1.4–2.8 (10H, cyclic $CH_2$'s and alphatic $CH_2$'s), 2.55(3H,s,CH₃CO) 3.79 (3H,s,OCH₃), 4.2 (2H,t,OAr), 4.2 (2H,t,OAr), 4.7 (1H,m,CH—OAr), 6.4–7.6(5-H,ArH's).

(d) Compound 6c (250 mg) was dissolved in distilled acetone (5 ml) containing potassium hydroxide (41.8 mg) and dimethyl sulfate (117.6 mg). The mixture was heated with stirring under argon at 40° C. for 10 hours. The mixture was cooled, the solvent removed and the residue partitioned between ethyl acetate and water. The organic layer was separated and dried over magnesium sulfate. Evaporation of the volatiles in vacuo afforded 240 mg of product, methyl 7-[3-(4-acetyl-3-methoxy-2-propylphenoxy)propoxy]-3,4-dihydro-8-propyl-2H-1-benzopyran-2-carboxylate, (6d) which was homogeneous by thin layer chromotography.

NMR $^1$H($\delta$, CDCl₃) 3.65 (3H, s, OCH₃).

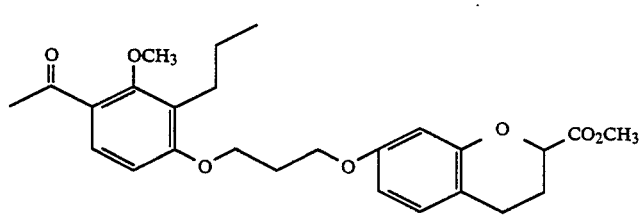
6d (e) Compound 6d (200 mg) was dissolved in methanol (3 ml) containing lithium hydroxide (1.0 ml of a 1M solution) and the mixture was stirred at room temperature for 10 hours. The solvent was removed and the residue partitioned between ethyl acetate and dilute hydrochloric acid. The organic layer was separated, washed with brine and dried over sodium sulfate. Evaporation of the volatiles in vacuo afforded 40 mg of product, 7-[3-(4-acetyl-3-methoxy-2-propylphenoxy)-propoxy]-3,4-dihydro-2H-1-benzopyran-2-carboxylic acid, as a gum.

Microanalysis: Found C 67.59, H 6.93. Calculated for

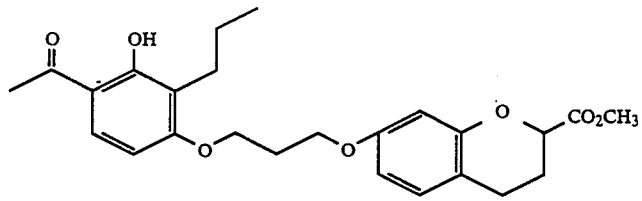
6c

C₂₅H₃₀O₇, C 67.86, H 6.83.

EXAMPLE 7

7-[3-(4-acetyl-3-methoxy-2-propylphenoxy)propoxy]-4-oxo-8-propyl-4H-1-benzopyran-2-carboxylic acid.

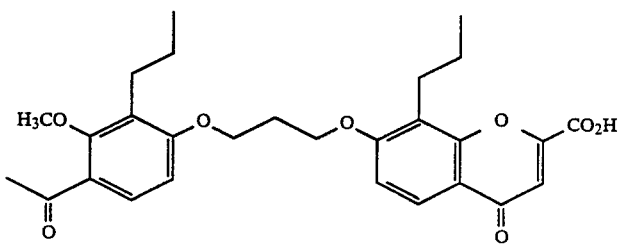

(a) Methyl 7-[3-(4-acetyl-3-hydroxy-2-propylphenoxy)propoxy]-4-oxo-8-propyl-4H-1-benzopyran-2-carboxylate (250 mg, 0.48 mMol) was dissolved in acetone (10 ml) containing potassium hydroxide (35 mg, 0.53 mMol), and dimethyl sulfate (78.3 mg 0.62 mMol). The mixture was heated at reflux temperature for 10 hours and then cooled. The residue was partitioned between ethyl acetate and water and the organic layer separated and dried over sodium sulfate. The solvent was removed in vacuo to afford 260 mg of product, methyl 7-[3-(4-acetyl-3-methoxy-2-propylphenoxy)propoxy]-4-oxo-8-propyl-4H-1-benzopyran-2-carboxylate.

NMR: $^1$H($\delta$, CDCl₃) 0.9(6H, 2t's, propyl CH₃'s), 1.4–2.8 (10H, alphatic CH₂'s), 3.75(3H,s,OCH₃ ether), 4.0(3H,s,CH₃ ester), 4.25(2H,t,CH₂OAr), 4.35 (2H,t,CH₂OAr) 7.05(1H,s, olefinic H) 6.7, 7.05, 7.55 and 8.05 (4H, d's, Ar H's).

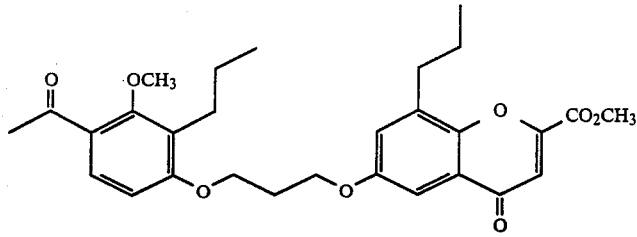

7a (b) Compound 7a (200 mg, 0.4 mMol) was dissolved in methanol (2 ml) containing 0.48 ml of a 1M lithium hydroxide solution. The mixture was stirred at room temperature for 10 hours and the solvent removed. The residue was partitioned between ethyl acetate and dilute hydrochloric acid and the organic layer was separated, dried over magnesium sulfate, filtered and evaporated in vacuo. The product, 7-[3-(4-acetyl-3-methoxy-2-propylphenoxy)propoxy]-4-oxo-8-propyl-4H-1-benzopyran-2-carboxylic acid, was isolated as a light yellow gum (122 mg, 62% yield). Microanalysis: Found C 66.43, H 6.59. Calculated for $C_{28}H_{32}lO_8 \cdot \frac{1}{2}H_2O$; C 66.43, H 6.59.

EXAMPLE 8

7-[3-(4-acetyl-3-methoxy-2-propylphenoxy)propoxy]-3,4-dihydro-N-methyl-8-propyl-2H-1-benzopyran-2-carboxamide.

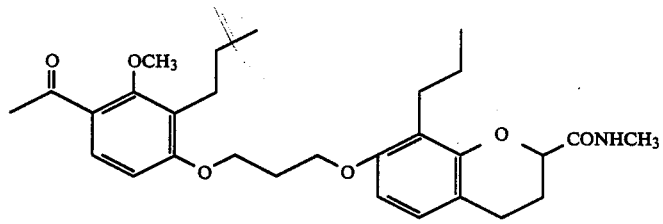

The compound of Example 1 (80 mg,) was treated with a slight excess of oxalyl chloride and the mixture left to stand at room temperature for 2 hours. The mixture was stripped, dissolved in methylene chloride and methylamine gas was bubbled into the reaction mixture. The mixture was washed with water, dried over magnesium sulfate filtered and the solvent was evaporated in vacuo. The resultant white solid was washed with ethyl acetate/hexane (2:8) and dried in vacuo. 60 mg of product was obtained. Microanalysis: Found C 69.63, H 7.96, N 2.86, Calculated for $C_{29}H_{39}NO_6$, C 70.00, H 7.9, N 2.82.

EXAMPLE 9

Methyl 7-[[5-(4-acetyl-3-methoxy-2-propylphenoxy)pentyl]oxy]-3,4-dihydro-8-propyl-2H-1-benzopyran-2-carboxylate

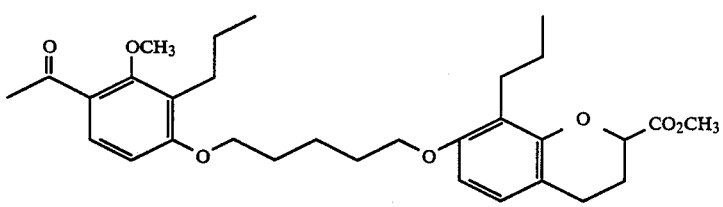

Methyl 7-[[5-(4-acetyl-3-hydroxy-2-propylphenoxy)pentyl]oxy]-3,4-dihydro-8-propyl-2H-1-benzopyran-2-carboxylate (1 mMol), prepared as described in U.S. Pat. No. 4,565,882, was dissolved in acetone containing 2.5 equivalents of potassium hydroxide and 3 equivalents of dimethyl sulfate. The mixture was heated at 40° C. for 10 hours and then cooled; the solvent was removed in vacuo and the residue partitioned between ethyl acetate and water. The organic layer was separated and dried over magnesium sulfate. Evaporation of the volatiles in vacuo afforded the methyl ether.

NMR $^1H(\delta, CDCl_3)$ 0.9 (6H, 2t's, propyl $CH_3$'s), 1.4–2.8(18H, aliphatic and cyclic $CH_2$'s), 2.55 (3H,s, $CH_3CO$), 3.75 (3H, s, $OCH_3$) 3.85 (3H, s, $OCH_3$), 3.9 (2H, t, $CH_2OAr$), 4.1 (2H, t, $CH_2OAr$), 4.7 (1H, dd CHOAr), 6.4, 6.65, 6.8, and 7.55 (4H, ArH's).

The compounds of Examples 10 to 14 were prepared according to the procedure described in Example 9 beginning with the appropriate phenol.

EXAMPLE 10

Methyl 7-[3-(4-acetyl-3-methoxy-2-propylphenoxy)propoxy]-3,4-dihydro-2-methyl-4-oxo-8-propyl-2H-1-benzopyran-2-propanoate

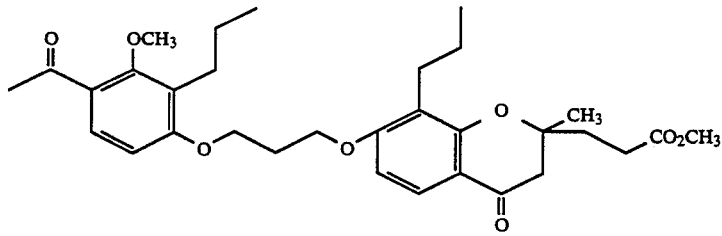

The title compound was prepared according to the method of Example 9 from methyl 7-[3(4-acetyl-3-hydroxy-2-propylphenoxy)propoxy]-3,4-dihydro-2-methyl-4-oxo-8-propyl-2H-1-benzopyran-2-propanoate, which was prepared as described in U.S. Pat. No. 4,665,203.

NMR $^1$H($\delta$,CDCl$_3$) 0.9(6H, 2ts, propyl CH$_3$'s), 1.4–2.7 (16H, aliphatic and cyclic CH$_2$'s), 1.35 (3H,s,CH$_3$), 2.6(3H, s, CH$_3$CO), 3.7(3H, s, OCH$_3$), 3.75 (3H,s, OCH$_3$), 4.25 (4H, CH$_2$OAr), 6.6, 6.7, 7.6 and 7.75 (4H, d's, ArH's).

EXAMPLE 11

Methyl 7-[[4-(4-acetyl-3-methoxy-2-propylphenoxy)-2-butynyl]oxy]-3,4-dihydro-2-methyl-4-oxo-8-propyl-2H-1-benzopyran-2-propanoate

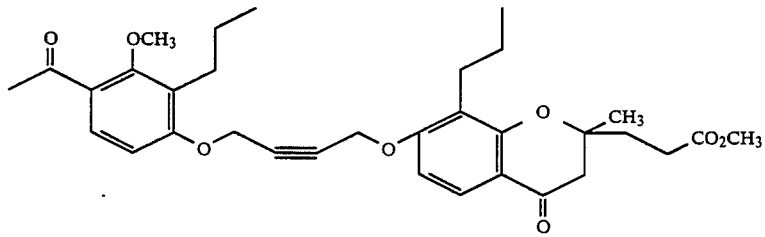

The title compound was prepared by the method of Example 9 from methyl 7-[[4-(4-acetyl-3-hydroxy-2-propylphenoxy)-2-butynyl]oxy]-3,4-dihydro-2-methyl-4-oxo-8-propyl-2H-1-benzopyran-2-propanoate.

NMR $^1$H($\delta$,CDCl$_3$) 0.9 (6H, 2t's, propyl CH$_3$'s), 1.4–2.7 (14H, aliphatic and cyclic CH$_2$'s), 1.35 (3H, s, CH$_3$), 2.6 (3H, s, CH$_3$CO), 3.7 (3H, s, OCH$_3$), 3.75 (3H, s, OCH$_3$), 4.8 (4H, s, CH$_2$OAr) 6.6, 6.7, 7.65 and 7.75 (4H, d's, ArH's).

EXAMPLE 12

Methyl 7-[3-(4-acetyl-3-methoxy-2-propylphenoxy)propoxy]-1,2,3,4-tetrahydro-8-propyl-2-naphthalenecarboxylate

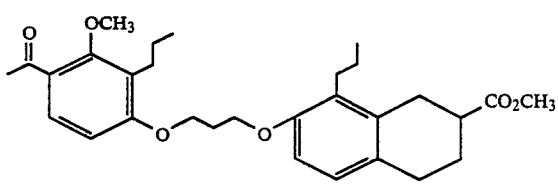

(a) 1.6 grams of 3-(2-n-propyl-3-hydroxy-4-acetylphenoxy)-1-bromopropane (.005 mole) which was prepared as described in U.S. Pat. No. 4,565,882 (Miyano et al.) was dissolved in 30 ml of methyl ethyl ketone. Two grams (2.5 equivalents) of potassium carbonate was added to the reaction along with 1.25 grams (.005 mole) of methyl 1,2,3,4-tetrahydro-7-hydroxy-8-propyl-2-naphthalenecarboxylate obtained in Example 28. After 100 mg of sodium iodide was added, a nitrogen blanket was placed on the system and the contents were refluxed for forty-eight hours. The reaction was cooled to room temperature. The mixture was filtered and the filtrate evaporated. The residue was chromatographed on silica gel with elution by 3% acetone-toluene. Eluant evaporation left 1.45 grams (60%) of compound (12a), methyl 7-[3-(4-acetyl-3-hydroxy-2-propylphenoxy)propoxy]-1,2,3,4-tetrahydro-8-propyl-2-naphthalenecarboxylate, m.p. 84°–85° C.

Microanalysis: Calc: C, 72.17; H, 7.94; for C$_{29}$H$_{38}$O$_6$. Found: C, 71.87; H, 7.90.

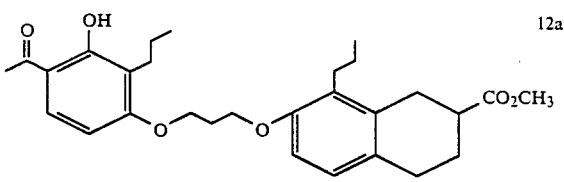

12a (b) The title compound was prepared by the method of Example 9 from methyl 7-[3-(4-acetyl-3-hydroxy-2-propylphenoxy)propoxy]-1,2,3,4-tetrahydro-8-propyl-2-napthalenecarboxylate.

1-oxopropyl)-2-propylphenoxy]-propoxy-8-propyl-2H-1-benzopyran-2-carboxylate, as an oil.

Microanalysis: Calc: C, 70.08; H, 7.86; Found: C, 69.51; H, 7.81.

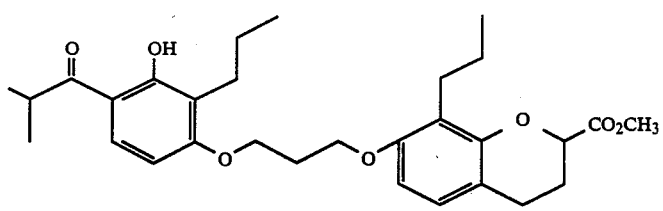

13a

NMR $^1$H($\delta$,CDCl$_3$) 0.95(6H, 2t's, propyl CH$_3$'s), 1.4–3.1 (16H, aliphatic and cyclic CH$_2$'s), 2.6 (3H, s, CH$_3$CO), 3.75 (6H, 2 overlapping singlets, OCH$_3$'s), 4.5 (2H, t, CH$_2$OAr), 4.25 (2H, t, CH$_2$OAr), 6.7, 6.9, 7.55 (4H, Ar H's).

EXAMPLE 13

Methyl 3,4-dihydro-7-[3-[3-methoxy-4-(2-methyl-1-oxopropyl)-2-propylphenoxy]propoxy]-8-propyl-2H-1-benzopyran-2-carboxylate (b) The title compound was prepared by the method of Example 9 from methyl 3,4-dihydro-7-[3-[3-hydroxy-4-(2-methyl-1-oxopropyl)-2-propylphenoxy]-propoxy]-8-propyl-2H-1-benzopyran-2-carboxylate.

NMR $^1$H($\delta$,CDCl$_3$) 0.9(6H, 2t's, propyl CH$_3$'s), 1.15 (6H, d, (CH$_3$)$_2$CCO), 1.4–2.7 (14H, aliphatic and cyclic CH$_2$'s), 3.7 (3H,s, OCH$_3$) 3.75 (3H, s, OCH$_3$), 4.15, 4.2 (4H, 2t's, CH$_2$OAr), 4.75 (1H, 1dd, CHOAr), 6.4, 6.7, 6.8 and 7.35 (4H, d's, ArH's).

EXAMPLE 14

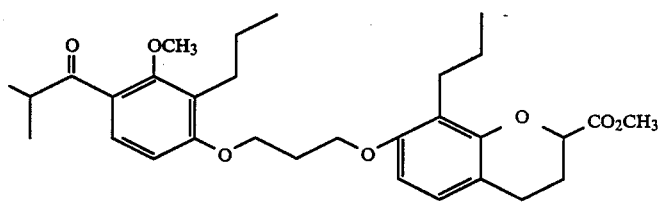

(a) A solution of 495 mg (1.89 mMole) of triphenylphosphine, 420 mg (1.89 mMole) of 2,4-dihydroxy-3-propylisobutyrophenone, 582 mg (1.89 mMole) of methyl 7-(3-hydroxypropoxy)-8-n-propylchroman-2-carboxylate in 5 ml of tetrahydrofuran was prepared and cooled in an ice bath. Diethyl azocarboxylate, 350 mg (1.89 mMole) was added and the solution was allowed to warm to room temperature and stir for 18 hours.

The solvent was removed by rotary evaporation and the residue triturated with 25 ml ether, cooled and filtered. The ether filtrate was then washed with water, brine, and dried over anhydrous magnesium sulfate. The drying agent was removed by filtration, the ether removed by rotary evaporation, and the residue purified by elution chromatography on silica gel with 1% acetone-toluene to furnish 720 mg (75%) of the desired ester, methyl 3,4-dihydro-7-[3-[3-hydroxy-4-(2-methyl- Ethyl 7-[3-(4-acetyl-3-methoxy-2-propylphenoxy)-propoxy]-3,4-dihydro-8-propyl-2H-1-benzopyran-2-propanoate.

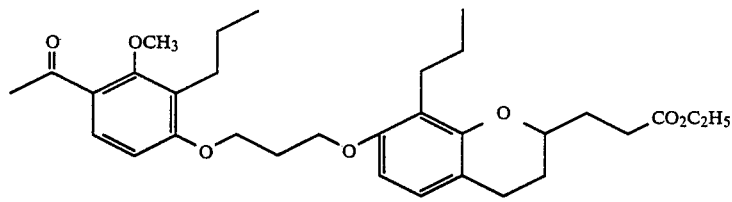

The title compound was prepared by the method of Example 9 from ethyl 7-[3-(4-acetyl-3-hydroxy-2-propylphenoxy)propoxy]-3,4-dihydro-8-propyl-2H-1-benzopyran-2-propanoate which was prepared as described in U.S. Pat. No. 4,665,203.

NMR $^1$H($\delta$,CDCl$_3$) 0.9 (6H, 2ts, propyl CH$_3$'s), 1.2–2.7 (20H, aliphatic cyclic and CO$_2$CH$_2$CH$_3$ H's), 2.6 (3H, s, CH$_3$CO), 3.75 (3H, s, OCH$_3$), 4.0 (1H, m, CHOAr), 4.1, 4.3 (4H, 2 triplets, CH$_2$OAr), 6.4, 6.7, 6.8, 7.55 (4H, ArH's).

EXAMPLE 15

7-[[5-(4-acetyl-3-methoxy-2-propylphenoxy)pentyl]oxy]-3,4-dihydro-8-propyl-2H-1-benzopyran-2-carboxylic acid.

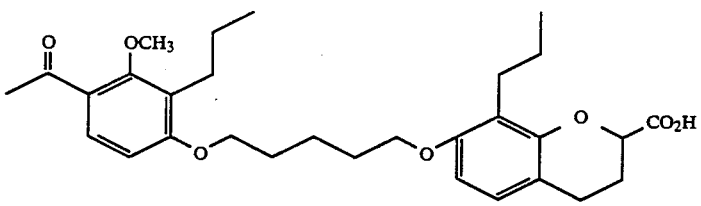

The compound prepared in Example 9 (1 mMol) was dissolved in methanol containing two equivalents of a 1M lithium hydroxide solution in water. The mixture was stirred at room temperature for 10 hours and then solvent was removed in vacuo. The residue was partitioned between ethyl acetate and water, the organic layer was separated and dried over magnesium sulfate and the volatiles were removed in vacuo. The product carboxylic acid may be purified by column chromatography on silica gel if necessary.

NMR $^1$H($\delta$, CDCl$_3$) 0.9(6H, 2ts, propyl CH$_3$'s), 1.4–2.8 (18H, aliphatic and cyclic CH$_2$'s), 2.55 (3H, s, CH$_3$CO), 3.75(3H, s, OCH$_3$), 3.9(2H, t, CH$_2$OAr), 4.1 (2H, t, CH$_2$OAr) 4.75(1H, m, CHOAr), 6.4, 6.65, 6.8, and 7.55 (4H, ArH's).

EXAMPLE 16

7-[3-(4-acetyl-3-methoxy-2-propylphenoxy)propoxy]-3,4-dihydro-2-methyl-4-oxo-8-propyl-2H-1-benzopyran-2-propanoic acid

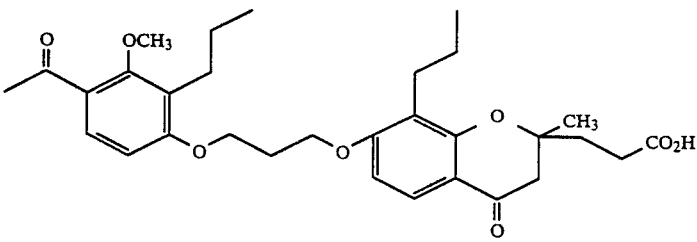

The title compound was prepared from the compound of Example 10 using the method of Example 15.

Microanalysis: Found: C 68.55, H 7.60. Calculated for C$_{31}$H$_{40}$O$_8$: C 68.87, H 7.46.

EXAMPLE 17

7-[[4-(4-acetyl-3-methoxy-2-propylphenoxy)propoxy]-2-butynyl]oxy]-3,4-dihydro-2-methyl-4-oxo-8-propyl-2H-1-benzopyran-2-propanoic acid

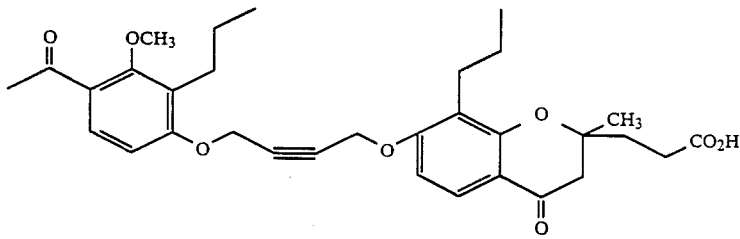

The title compound was prepared from the compound of Example 11 using the method of Example 15.

NMR $^1$H ($\delta$, CDCl$_3$) 0.9 (6H, 2t's, propyl CH$_3$'s), 1.4–2.7 (14H, aliphatic and cyclic CH$_2$'s), 1.35 (3H, s CH$_3$), 2.6 (3H, s, CH$_3$CO), 3.75 (3H, s, OCH$_3$), 4.85 (4H, brs, CH$_2$OAr), 6.6, 6.7, 7.6 and 7.75 (4H, d's, ArH's).

EXAMPLE 18

7-[3-(4-acetyl-3-methoxy-2-propylphenoxy)propoxy]-1,2,3,4-tetrahydro-8-propyl-2-naphthalenecarboxylic acid

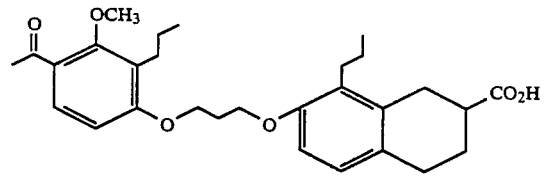

The title compound was prepared from the compound of Example 12 using the method of Example 15.

Microanalysis: Found: C 71.85, H 7.94. Calculated for C$_{24}$H$_{38}$O$_6$: C 72.17, H 7.94.

EXAMPLE 19

3,4-dihydro-7-[3-[3-methoxy-4-(2-methyl-1-oxopropyl)-2-propylphenoxy]propoxy]-8-propyl-2H-1-benzopyran-2-carboxylic acid

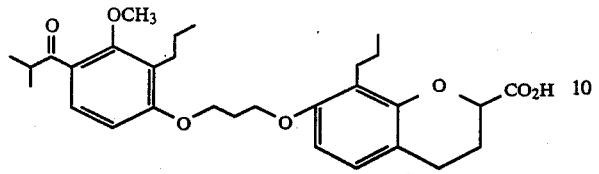

The title compound was prepared from the compound of Example 13 using the method of Example 15.
NMR $^1$H($\delta$, CDCl$_3$) 0.9 (6H, 2t's, propyl CH$_3$'s), 1.15 (6H, d, (CH$_3$)$_2$CCO), 1.4–2.7 (14H, aliphatic and cyclic CH$_2$'s), 3.7 (3H, s, OCH$_3$), 4.15, 4.2 (4H, 2t's, CH$_2$OAr) 4.75 (1H, dd, CHOAr), 6.4, 6.7, 6.82 and 7.35 (4H, d's, ArH's).

EXAMPLE 20

7-[3-(4-acetyl-3-methoxy-2-propylphenoxy)propoxy]-3,4-dihydro-8-propyl-2H-1-benzopyran-2-propanoic acid

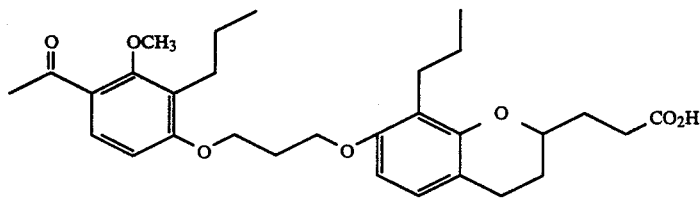

The title compound was prepared from the compound of Example 14 using the method of Example 15.
NMR $^1$H ($\delta$, CDCl$_3$) 0.9 (6H, 2ts, propyl CH$_3$'s), 1.2–2.7 (18H, aliphatic and cyclic CH$_2$'s), 2.6 (3H, s, CH$_3$CO) 3.75 (3H, s, OCH$_3$), 4.0 (1H, m, CHOAr), 4.1, 4.3 (4H, 2t's, CH$_2$OAr), 6.4, 6.7, 6.8, 7.55 (4H, ArH's).

EXAMPLE 21

7-[3-(4-acetyl-3-ethoxy-2-propylphenoxy)-propoxy]-3,4-dihydro-8-propyl-2H-1-benzopyran-2-carboxylic acid

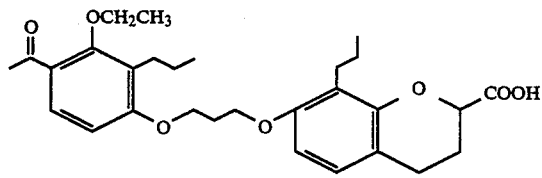

(a) 4-(3-chloropropoxy)-2-hydroxy-3-propylacetophenone (5.0 g, 18.47 mMol), potassium carbonate (7.3 g), and iodoethane (3.0 ml) were dissolved in dry DMF (50 ml) and the mixture stirred overnight at room temperature. The reaction mixture was then partitioned between ether and water and the organic layer separated. The ether extracts were washed with water and brine and then dried over sodium sulfate. Evaporation of the volatiles in vacuo afforded 5.36 g of crude 4-(3-chloropropoxy)-2-ethoxy-3-propylacetophenone.

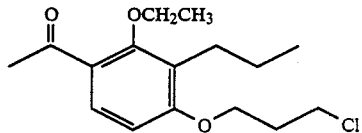

(b) 4-(3-chloropropoxy)-2-ethoxy-3-propylacetophenone (5.36 g) was dissolved in acetone containing 10 equivalents of sodium iodide, and the mixture was refluxed under nitrogen for 10 hours. Solvent was removed in vacuo and the residue partitioned between ether and water. The organic extracts were washed with water and brine, dried over sodium sulfate and evaporated in vacuo to afford 7.0 g of a yellow oil, 4-(3-iodopropoxy)-2-ethoxy-3-propylacetophenone.
NMR $^1$H ($\delta$, CDCl$_3$) 300 MH$_z$ 3.4 (2H, t, CH$_2$I).

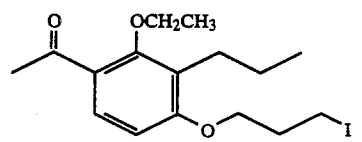

(c) Compound 21b (2.34 g, 6 mMol), methyl 7-hydroxy-8-propylchroman-2-carboxylate (1.25 g, 5 mMol) and potassium carbonate (2.07 g, 15 mMol) were suspended in dry DMF (12.5 ml) and the mixture stirred at room temperature for 48 hours. The mixture was then partitioned between ether and water and the ether layer separated, washed with water and brine and then dried over sodium sulfate. Evaporation of the volatiles in vacuo afforded 2.9 g of crude product which was purified by chromatography on silica gel to afford 1.34 g of pure methyl 7-[3-(4-acetyl-3-ethoxy-2-propylphenoxy)-propoxy]-3,4-dihydro-8-propyl-2H-1-benzopyran-2-carboxylate.

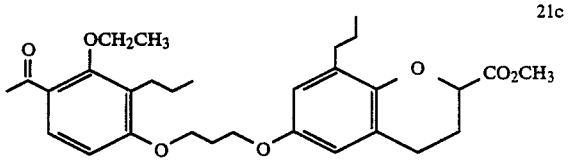

(d) Compound 21c (0.8 g, 1.56 mMoles) was dissolved in methanol/water (7:3, 25 ml) containing lithium hydroxide (0.13 g, 3.12 mMol). The mixture was stirred at room temperature for 2 hours and then partitioned between dilute hydrochloric acid and ether. The organic layer was separated, washed with brine, dried over sodium sulfate and concentrated in vacuo to afford 1.1 g of crude product. This material was purified by chromatography on silica gel using ethyl acetate/hexane/acetic acid (50:50:1) as eluant. 7-[3-(4-acetyl-3-ethoxy-2-propylphenoxy)-propoxy]-3,4-dihydro-8-propyl-2H-1-

EXAMPLE 22

7-[3-(4-acetyl-3-methoxy-2-propylphenoxy)propoxy]-4-oxo-8-propyl-4H-1-benzopyran-2-propanoic acid

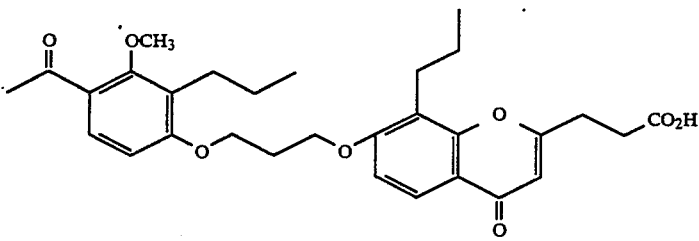

Starting with methyl 7-[3-(4-acetyl-3-hydroxy-2-propylphenoxy)propoxy]-4-oxo-8-propyl-4H-1-benzopyran-2-propanoate and following the procedure of Example 9 gave methyl 7-[3-(4-acetyl-3-methoxy-2-propylphenoxy)propoxy]-4-oxo-8-propyl-4H-1-benzopyran-2-propanoate which was hydrolyzed using the procedure of Example 15 to give the title compound.

Microanalysis: Calculated: C, 68.62; H, 6.92. Found: C, 68.24; H, 6.92.

EXAMPLE 23

Methyl 7-[[4-(4-acetyl-3-hydroxy-2-propylphenoxy)-2-butynyl]oxy]-3,4-dihydro-2-methyl-4-oxo-8-propyl-2H-1-benzopyran-2-propanoate

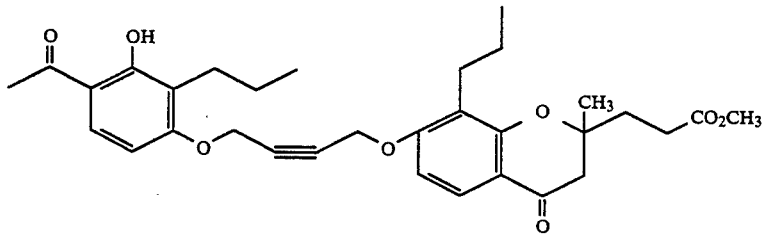

A solution of 2.04 g (7.8 mMole) of 4-(4-hydroxy-2-butynyloxy)-2-hydroxy-3-propylacetophenone, 2.49 g (7.8 mMole) of methyl -(3,4-dihydro-7-hydroxy-2-methyl-4-oxo-8-propyl-2H-1-benzopyran-2-yl)propanoate, and 2.04 g (7.8 mMole) of triphenylphosphine was prepared in 50 ml of dry tetrahydrofuran. After addition of 1.22 ml (7.8 mMole) of diethyl diazodicarboxylate the solution was stirred for 18 hours.

The tetrahydrofuran was removed by rotary evaporation and the residue stirred in 50 ml of ether. Insoluble solids were removed by filtration and the ether filtrate was concentrated by rotary evaporation to give 5.94 g of a crude oil. The oil was purified by elution chromatography to furnish 3.2 g (73%) of the methyl ester product.

Microanalysis: Calculated: C, 70.19; H, 7.14. Found: C, 70.33; H, 7.18.

EXAMPLE 24

Trans-methyl 7-[[4-(4-acetyl-3-hydroxy-2-propylphenoxy)-2-butenyl]oxy]-3,4-dihydro-2-methyl-4-oxo-8-propyl-2H-1-benzopyran-2-propanoate

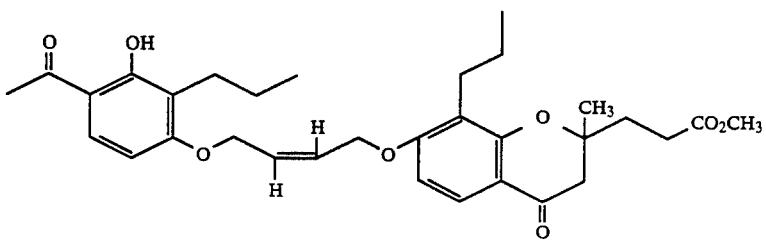

A solution of 3.05 g (11.5 mMole) trans-4-(4-hydroxy-2-butenyloxy)-2-hydroxy-3-propylacetophenone, 3.70 g (11.5 mMole) of methyl 3-(3,4-dihydro-7-hydroxy-2-methyl-4-oxo-8-propyl-2H-1-benzopyran-2-yl)propanoate, and 3.03 g (11.5 mMole) of triphenylphosphine in 75 ml of dry tetrahydrofuran was prepared. Diethyl diazodicarboxylate, 1.80 ml (11.5 mMole), was added and the solution was stirred for 18 hours at room temperature.

Solvent was removed from the reaction mixture by rotary evaporation and 75 ml of ether was added to the residue and stirred. After removal of insoluble solids by filtration, the ether filtrate was removed by rotary evaporation. The resulting crude material was purified by silica gel elution chromatography with 7% ethyl acetate-toluene to furnish 4.73 g (73%) of the methyl ester as an oil.

Microanalysis: Calculated: C, 69.94; H, 7.47. Found: C, 70.02; H, 7.45.

EXAMPLE 25

Trans-7-[[4-(4-acetyl-3-methoxy-2-propylphenoxy)-2-butenyl]oxy]-3,4-dihydro-2-methyl-4-oxo-8-propyl-2H-1-benzopyran-2-propanoic acid

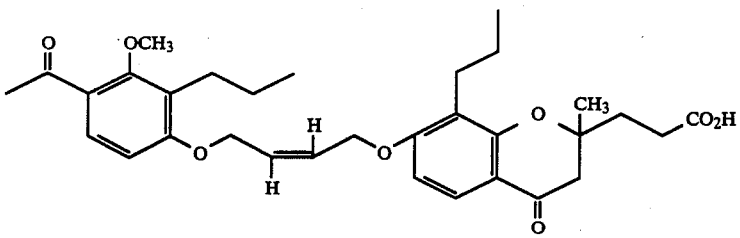

The compound of Example 24 is methylated using the method of Example 9 to give 7-[[4-(4-acetyl-3-methoxy-2-propylphenoxy)-2-butenyl]oxy]-3,4-dihydro-2-methyl-4-oxo-8-propyl-2H-1-benzopyran-2-propanoate which is then hydrolyzed using the method of Example 15 to give the title compound.

EXAMPLE 26

Cis-methyl 7-[[4-(4-acetyl-3-hydroxy-2-propylphenoxy)-2-butenyl]oxy]-3,4-dihydro-2-methyl-4-oxo-8-propyl-2H-1-benzopyran-2-propanoate

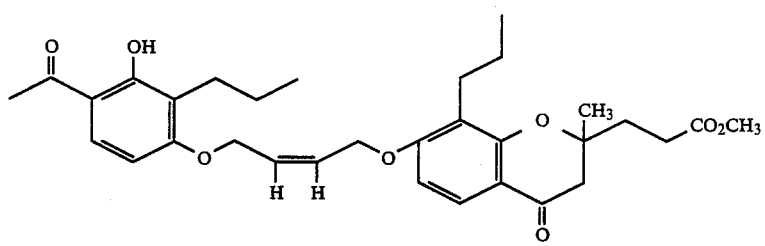

A solution of 5.82 g (22 mMole) of cis-4-(4-hydroxy-2-butenyloxy)-2-hydroxy-3-propylacetophenone, 7.05 g (22 mMole) of methyl-(3,4-dihydro-7-hydroxy-2-methyl-4-oxo-8-propyl-2H-1-benzopyran-2-yl)propanoate, and 5.77 g (22 mMole) of triphenylphosphine was prepared in 150 ml of dry tetrahydrofuran. After addition of 3.5 ml (22 mMole) of diethyl diazodicarboxylate, the mixture was stirred for 18 hours.

The tetrahydrofuran was removed by rotary evaporation and the residue stirred with 100 ml of ether. Insoluble solids were removed by filtration and the ether filtrate was concentrated by rotary evaporation to give 16.6 g of yellow oil. The oil was purified by silica gel chromatography using 10% ethylacetate-toluene to furnish 6.28 g (50%) of pure methyl ester product.

Microanalysis: Calculated: C, 69.94; H, 7.47. Found: C, 69.52; H, 7.36.

EXAMPLE 27

Cis-7-[[4-(4-acetyl-3-methoxy-2-propylphenoxy)-2-butenyl]-oxy]-3,4-dihydro-2-methyl-4-oxo-8-propyl-2H-1-benzopyran-2-propanoic acid

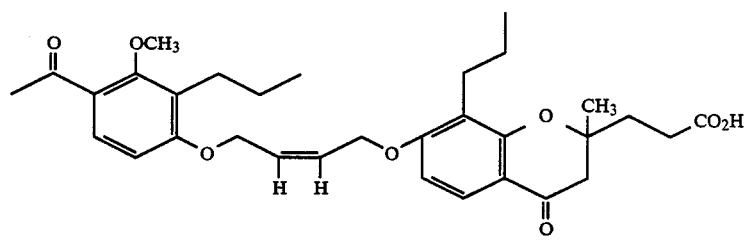

The compound of Example 26 is methylated using the method of Example 9 to give cis-methyl 7-[[4'-(4-acetyl-3-methoxy-2-propylphenoxy)-2-butenyl]]-oxy]-3,4-dihydro-2-methyl-4-oxo-8-propyl-2H-1-benzopyran-2-propanoate which is then hydrolyzed using the method of Example 15 to give the title compound.

EXAMPLE 28

(a) methyl 1,2,3,4-tetrahydro-7-methoxy-1-oxo-2-naphthalene carboxylate

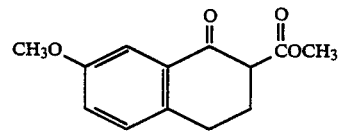

28a

A 50% slurry of NaH (30 g, 0.62 moles) in hexane was filtered through a fritted glass funnel to remove the mineral oil. The NaH was then added to a 2L flask, covered with 300 ml of tetrahydrofuran (THF), and placed under a $N_2$ atmosphere. Upon the addition of 0.62 moles of dimethyl carbonate at one time with stirring, the reaction mixture was heated to 40°–50° C., whereupon 50 g (0.28 moles) of commerically available 7-methoxy-1-tetralone in 150 ml of THF was added at a rate to minimize foaming (1 hr.). Afte refluxing the reaction mixture for 2 hrs., the solution (red) was cooled to room temperature and slowly acidified by the addition of 45 ml of acetic acid. The resulting paste was dissolved upon addition of 50 ml of water. Ether was added and the layers were separated. The organic phase was washed with H₂O, 3% NaHCO₃ solution, and dried (Na₂SO₄). After filtration, the solvent was evaporated on a rotary evaporator. The residue was distilled at 168°–170° C. at 0.2 mm Hg.

Analysis for $C_{13}H_{16}O_4$ (MW=236.26):
Calcd: C, 66.66; H, 6.02.
Found: C, 66.87; H, 6.07.

(b) methyl 1,2,3,4-tetrahydro-7-methoxy-2-naphthalenecarboxylate

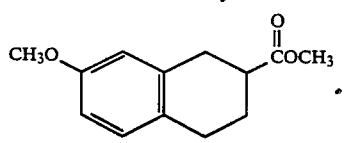

To 58 g (0.248 mole) of the product from Example 28(a) dissolved in a mixture of 387 ml of acetic acid and 16.6 ml of perchloric acid and placed in a 1L pressure bottle was added 5.8 g of 5% Pd/C. The bottle was placed in a Parr shaker and hydrogenated at R.T. at 30 p.s.i. for 2 hr. After filtration, the filtrate was diluted with 1.1 liter of CHCl₃, washed with H₂O until the pH was neutral (5×). The organic phase was dried (Na₂SO₄) and the solvent evaporated to produce 49 g of a crude yellow oil (the titled product).

Analysis for $C_{13}H_{16}O_3$ (MW=220.26):
Calcd: C, 70.88; H, 7.32.
Found: C, 70.62; H, 7.09.

(c) 1,2,3,4-tetrahydro-7-methoxy-2-naphthalenecarboxylic acid

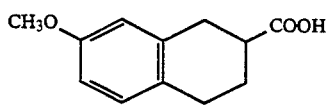

To 49 g (0.22 mole) of the product of Example 28(b) dissolved in 600 ml of methanol at R.T. was added 150 ml of 2M LiOH with stirring. After heating the stirred solution at 50° C. for 2 hr., the methanol was removed by rotary evaporation, the aqueous residue was washed 1× with ether, and acidified to pH 2 with HCl. Upon cooling and stirring, the crude acid precipitated and was separated by filtration. The crude acid was recrystallized from ether-hexane to give 30 g (67%) of the product, m.p. 119°–122° C.

Analysis for $C_{12}H_{14}O_3$ (MW=206.23):
Calcd: C, 69.98; H, 6.84.
Found: C, 96.70; H, 6.92.

(d) 1,2,3,4-tetrahydro-7-hydroxy-2-naphthalenecarboxylic acid

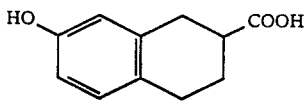

To a 500 ml flask containing 100 g of pyridine hydrochloride was added 30 g of the product of Example 28(c) and the reaction mixture was blanketed with N₂. The reaction mixture was placed in an oil bath and heated to 215° C. for 2 hr. Upon cooling to R.T., 200 ml of 1N HCl was added with stirring followed by 300 ml of 1:1 mixture of ether/ethyl acetate. The organic phase was separated, washed 3× with H₂O, dried (MgSO₄), and filtered. Upon evaporation of the solvent, the residue was recrystallized from ether/hexane to produce 21.4 g of the titled product, m.p. 170°–171° C.

Analysis for $C_{11}H_{12}O_3$ (MW=192.21):
Calcd: C, 68.73; H, 6.29.
Found: C, 68.58; H, 6.35.

(e) methyl 1,2,3,4-tetrahydro-7-hydroxy-2-naphthalenecarboxylate

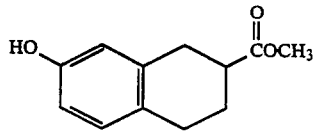

To 21 g of the product of Example 28(d) dissolved in 250 ml of methanol and placed in a 1L flask was added 30 ml of trimethylorthoformate and 8 ml of H₂SO₄. The flask was covered and allowed to stand at room temperature for 3 days. Upon rotary evaporation of the methanol, 500 ml of ether was added and the organic phase was washed 2× with 3% NaHCO₃ solution, and 2× with water. The organic phase was dried (Na₂SO₄), filtered, and the solvent removed by rotary evaporation. The residue was recrystallized from ethyl acetate-hexane to give 22 g of the product, m.p. 83°–84° C.

Analysis for $C_{12}H_{14}O_3$ (MW=206.24):
Calcd: C, 69.89; H, 6.84.
Found: C, 69.86; H, 6.82.

(f) methyl 1,2,3,4-tetrahydro-7-(2-propenyloxy)-2-naphthalenecarboxylate

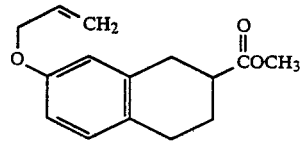

To 20 g (0.097 mole) of the product of Example 28(e) dissolved in 300 ml of dry acetone was added 35 g (2.5 eq.) of K₂CO₃ with vigorous stirring. An excess (20 g) of allyl bromide was then added to the reaction vessel and the mixture was refluxed with a drying tube attached for 1 day. The reaction mixture was filtered and the solvent in the filtrate evaporated by rotary evaporation. The residue was taken up in 50 ml of toluene and chromatographed on a 500 g silica gel flash column, eluting with toluene. The eluent was evaporated and 17.5 g (78%) of the product was isolated as a clear oil.

Analysis for $C_{15}H_{18}O_3$ (MW=246.31):
Calcd: C, 73.15; H, 7.37.
Found: C, 72.84; H, 7.44.

(g) methyl 1,2,3,4-tetrahydro-7-hydroxy-8-(2-prophenyl)-2-naphthalenecarboxylate

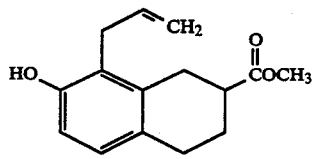

28g

To 20 g of diethylaniline in a reaction vessel was added under argon 17 g of the product of Example 28(f). After the reaction mixture was heated at 215° C. for 6 hr., thin-layer chromatography (TLC) showed that two products had formed. Upon cooling, the reaction contents were poured into a 3:1 mixture of ethyl acetate/ether and the resulting solution washed with 200 ml of 2N HCl and 100 ml of water. The organic layer was separated, dried ($Na_2SO_4$), and filtered. Upon removal of the solvent by rotary evaporation, the crude residue (17 g) was chromatographed on silica gel, eluting with 3% acetone/toluene. The most non-polar material (12.5 g) was the titled product, 28 g, mp. 90°–91° C. The most polar material was methyl 1,2,3,4-tetrahydro-7-hydroxy-6-(2-propenyl)-2-naphthalenecarboxylate.

Analysis for $C_{15}H_{18}O_3$ (MW=246.31):
Calcd: C, 73.15; H, 7.37.
Found: C, 73.01; H, 7.34.

(h) methyl 1,2,3,4-tetrahydro-7-hydroxy-8-propyl-2-naphthalenecarboxylate

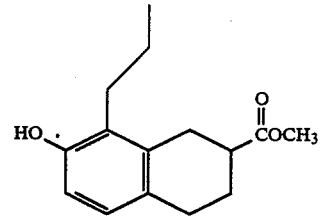

28h

To 12 g of the product of Example 28(g) dissolved in 125 ml of methanol and placed in a pressure bottle was added 1.25 g of 5% Pd/C. The bottle was placed in a Parr shaker and the mixture hydrogenated at room temperature and 2 p.s.i. for 1 hr. Upon filtration of the reaction mixture and evaporation of the solvent, 12 g of the product 28 h was produced as an oil.

Analysis for $C_{15}H_{20}O_3$ (MW=248.32):
Calcd: C, 72.55; H, 8.12.
Found: C, 71.83; H, 8.20.

EXAMPLE 29

7-[3-(4-acetyl-3-methoxy-2-propylphenoxy)propoxy]-3,4-dihydro-4-hydroxy-8-propyl-2H-1-benzopyran-2-propanoic acid

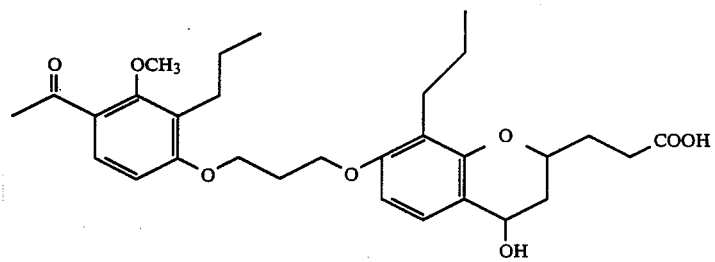

Starting with methyl 7-[3-(4-acetyl-3-hydroxy-2-propylphenoxy)propoxy]-3,4-dihydro-4-hydroxy-8-propyl-2H-b 1-benzopyran-2-propanoate prepared as disclosed in U.S. No. 4,665,203 and methylating the compound following the procedure of Example 9 then hydrolyzing that product according to the procedure of Example 15 gives the title compound.

Table 1 and Table 2 show test results for some embodiments of the invention. Table 3 shows the $LTD_4$ Receptor Binding test results.

TABLE 1

| | Receptor Binding | | | Degranulation |
|---|---|---|---|---|
| Compound | $LTB_4$ $IC_{50}$ | $LTD_4$[1] $IC_{50}$ | Chemotaxis[2] (Boyden) | $LTB_4$ $IC_{50}$ |
| Example 3 | $1.9 \times 10^{-7}$M | — | $IC_{50}, 2 \times 10^{-7}$M | $1.8 \times 10^{-7}$M |
| Example 4 | $5 \times 10^{-6}$M | — | 62% ($10^{-8}$M) | $2.7 \times 10^{-6}$M |
| Example 5 | $1 \times 10^{-7}$M | — | $IC_{50}, 0.5 \times 10^{-6}$M | $4 \times 10^{-7}$M |
| Example 6 | $2.6 \times 10^{-6}$M | Inactive | 48% ($10^{-6}$M) | $8 \times 10^{-6}$M |
| Example 7 | $0.5 \times 10^{-6}$M | Inactive | $IC_{50}, 3.6 \times 10^{-6}$M | $3.7 \times 10^{-6}$M |
| Example 8 | $1.8 \times 10^{-6}$M | — | 12% ($10^{-6}$M) | |
| Example 15 | $0.5 \times 10^{-6}$M | — | $IC_{50}, 6.6 \times 10^{-6}$M | $1.5 \times 10^{-6}$M |
| Example 16 | $0.25 \times 10^{-6}$M | Inactive | $IC_{50}, 0.65 \times 10^{-6}$M | $0.55 \times 10^{-6}$M |
| Example 17 | $0.8 \times 10^{-6}$M | — | 31% ($10^{-6}$M) | $2.1 \times 10^{-6}$M |
| Example 18 | $3.7 \times 10^{-7}$M | — | 87% ($10^{-5}$M) | $2.6 \times 10^{-6}$M |
| Example 19 | $1.2 \times 10^{-6}$M | — | 15% ($10^{-6}$M) | $5 \times 10^{-6}$M |
| Example 20 | $0.5 \times 10^{-6}$M | Inactive | $IC_{50}, 1.7 \times 10^{-6}$M | $0.4 \times 10^{-7}$M |
| Example 21 | $1 \times 10^{-6}$M | — | — | — |

TABLE 1-continued

| Compound | Receptor Binding | | | Degranulation |
| --- | --- | --- | --- | --- |
| | LTB$_4$ IC$_{50}$ | LTD$_4$[1] IC$_{50}$ | Chemotaxis[2] (Boyden) | LTB$_4$ IC$_{50}$ |
| Example 1 | 0.48 × 10$^{-6}$M | Inactive | IC$_{50}$,3 × 10$^{-6}$M | 1.5 × 10$^{-6}$M |
| Example 22 | 0.5 × 10$^{-6}$M | | IC$_{50}$,1.2 × 10$^{-6}$M | 1.6 × 10$^{-6}$M |

[1]Inactive means the compound tested was inactive at 10$^{-5}$M. These results are from Table 3.
[2]IC$_{50}$ is the effective concentration needed to cause 50% inhibition.

TABLE 2

| Compound | Guinea Pig Ileum Contraction pA$_2$ |
| --- | --- |
| Example 7 | 6.74 |
| Example 15 | Inactive |
| Example 20 | 6.5 |

TABLE 3

LTD$_4$ Receptor Binding[1]
LTB$_4$ Antagonist Testing Against an LTD$_4$ Receptor

| Compound [10 μM] | Percent Inhibition | | Activity |
| --- | --- | --- | --- |
| | Test #1 | Test #2 | |
| FPL 55712 | 54.68 | 46.96 | A |
| Example 1 | 4.07 | 16.40 | I |
| Example 20 | +12.96 | 23.51 | I |
| Example 16 | 16.49 | 24.08 | I |
| Example 7 | 28.90 | 34.40 | I |
| Example 6 | +1.63 | 25.97 | I |

[1]This method employs LTD$_4$ membrane receptors prepared from a male guinea pig lung homogenate which was aliquoted and stored at −70° C. The particular preparation used to test the compounds of Table 3 was GPLP 9, having a K$_D$ of 0.262 nM and yielding 0.447 pmol receptor/mg protein. Protein concentrations in these assays were adjusted to provide aproximately 0.1 nM receptor in the presence of lnM $^3$H-LTD$_4$. Incubation was conducted for 30 min. at 24° C. and filtration methods were used to separate bound from free ligand. Under these conditions, IC$_{50}$ values for LTD$_4$ and FPL 55712, a known LTD$_4$ receptor antagonist, were 1.71 × 10$^{-8}$M and 10.37 × 10$^{-6}$M respectively. All compounds tested were intially solubilized in DMSO. Each compound was evaluated at a dose of 10 μM (10$^{-5}$M) in triplicate in 2 separate assays. The percent inhibition of LTD$_4$ specific binding for each compound is shown in Table 3. By the criteria established for potential LTD$_4$ receptor antagonists, compounds are active if the 10 μM test concentration inhibits LTD$_4$ specific binding by 45% or more. Using this parameter, all the Table 3 compounds were considered inactive relative to FPL 55712.

Scheme A and Scheme B show two preferred synthesis routes for making the compound of Formula III.

Scheme C shows a general method for making compounds of the present invention.

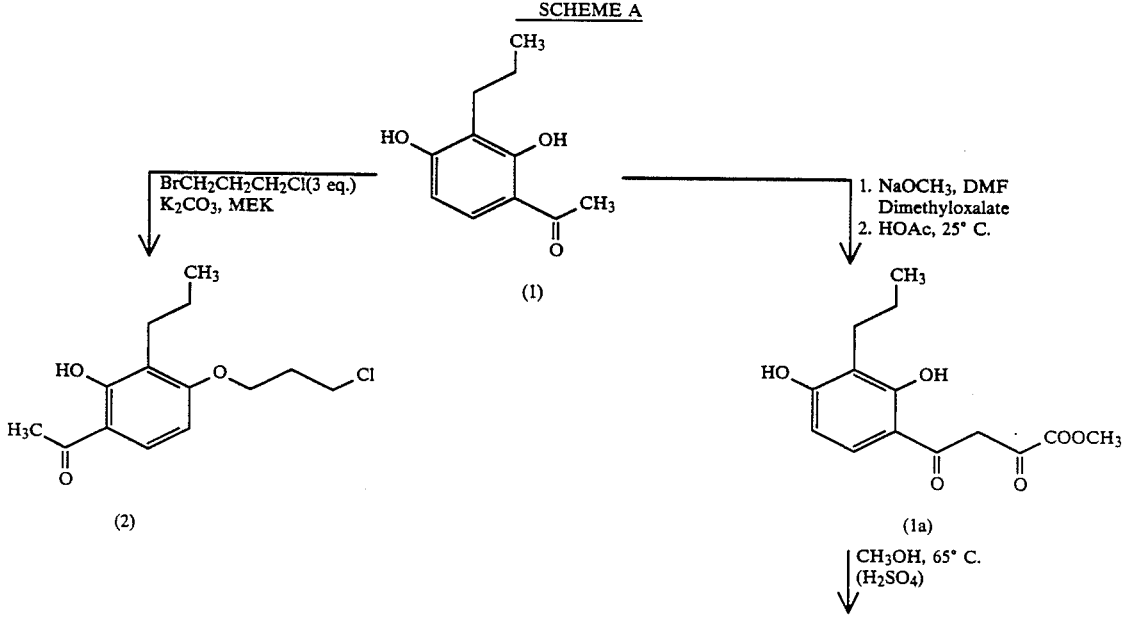

SCHEME A

SCHEME A
-continued
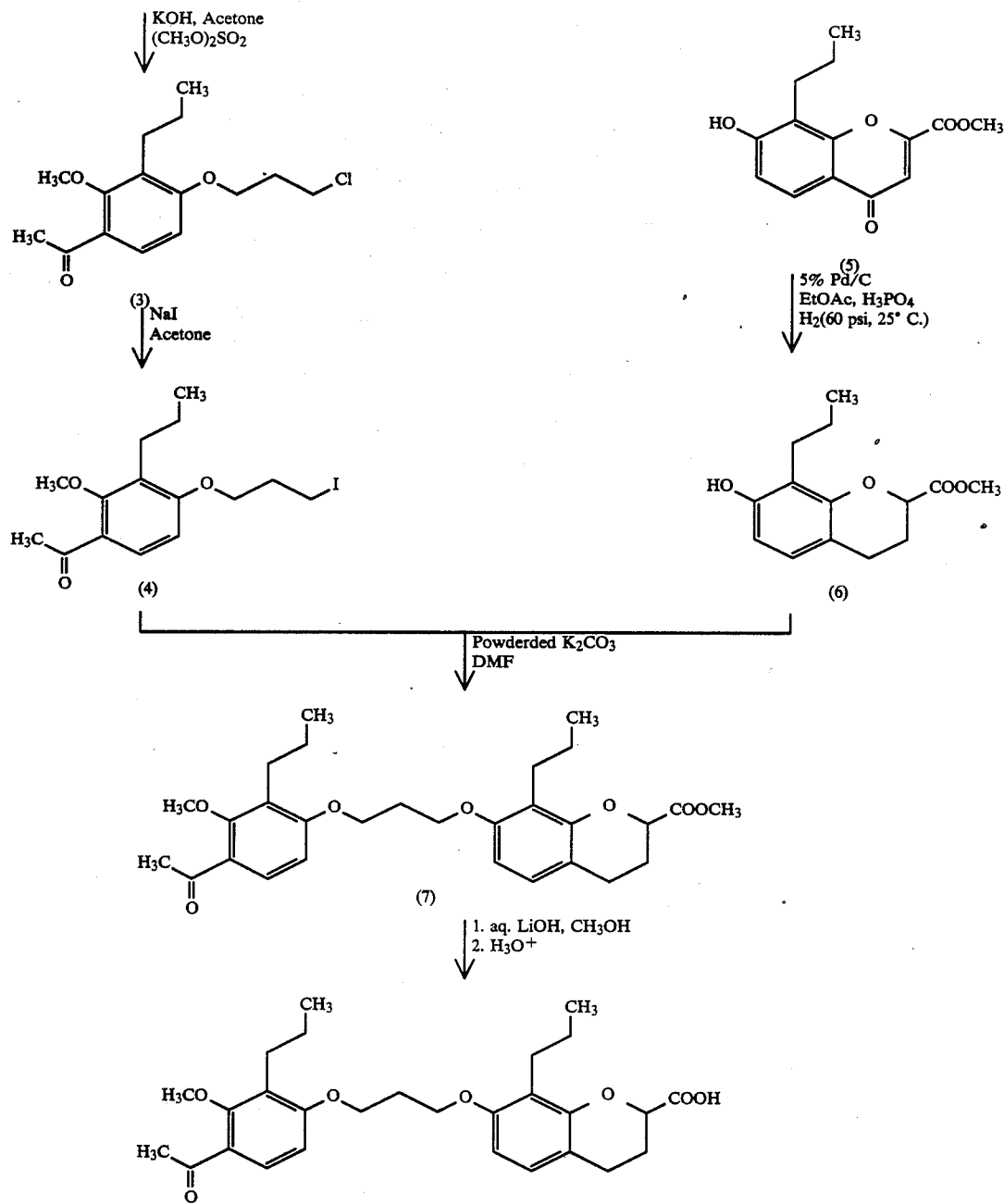
SCHEME B
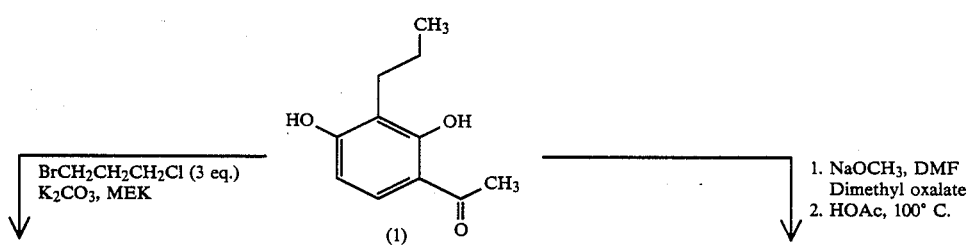

4,889,871
43    44
-continued
SCHEME B
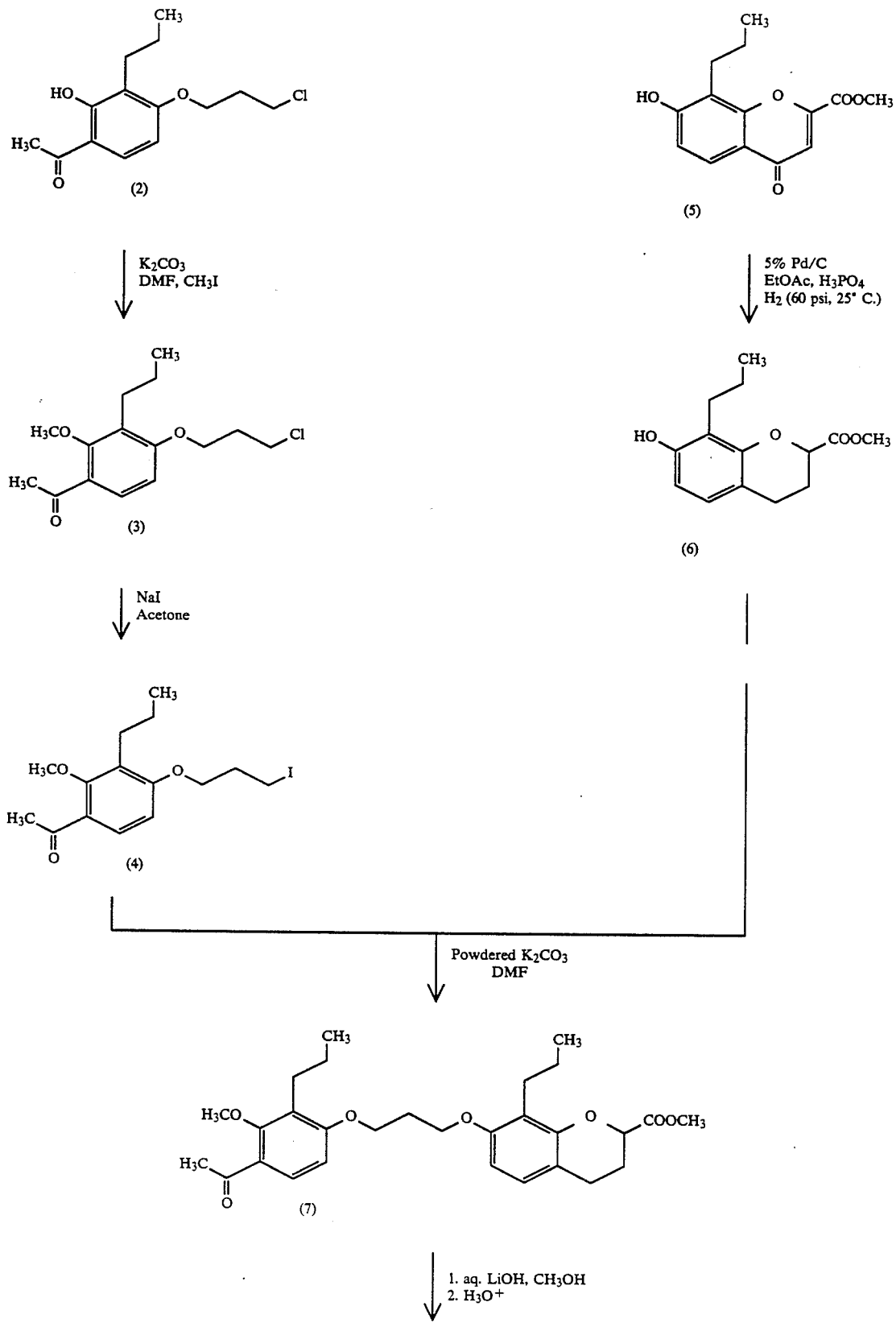

-continued
SCHEME B
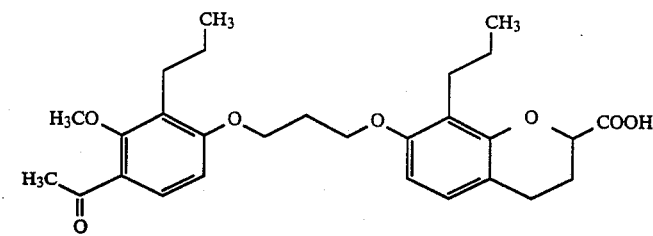
SCHEME C
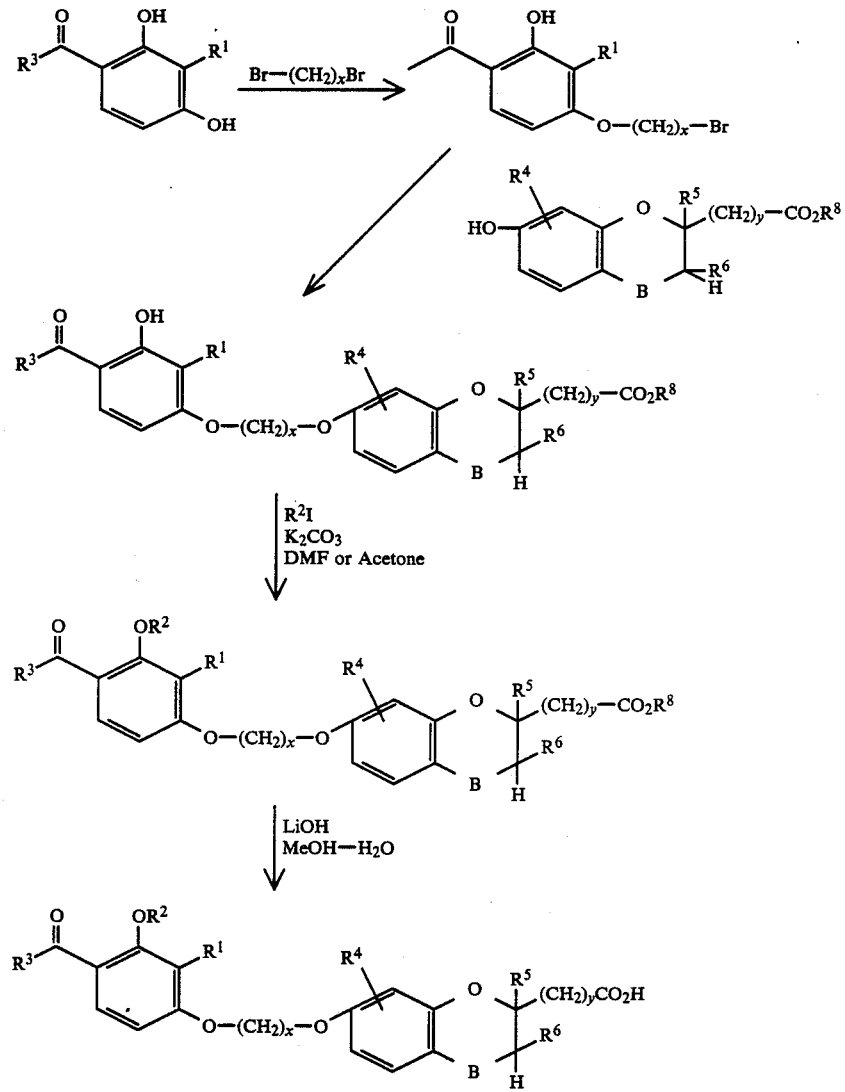
y = 0 to 6
x = 2 to 7
B = $CH_2$, C = O, C—OH
$R^2$ = methyl or ethyl
$R^3$ = alkyl
$R^5$ = H, alkyl or
$R^5$ and $R^6$ form a
carbon to carbon bond.
$R^4$ = H or alkyl
$R^1$ = alkyl, alkenyl, alkynyl, or
$(CH_2)_n$—R where n = 1 or 2
and R = cycloalkyl of 3-5
carbon atoms.
$R^8$ = alkyl
What is claimed is:
1. A compound of the formula:

[Structure: compound with R³-C(=O)- on benzene bearing OR² and R¹, connected via O-W-O to another benzene bearing R⁴, with ring containing Q, substituents R⁵, A, R⁶, H, and position B]

or a pharmaceutically acceptable salt thereof wherein
R¹ represents alkyl having 2-6 carbon atoms, alkenyl having 2 to 6 carbon atoms, alkynyl having 2 to 6 carbon atoms, or $(CH_2)_nR$ wherein R represents cycloalkyl of 3 to 5 carbon atoms l n is 1 or 2;
R² represents methyl or ethyl;
R³ represents alkyl having 1 to 5 carbon atoms;
W represents $(CH_2)_x$ where x is 2 to 7, alkenylene having 3 to 7 carbon atoms, alkynylene having 3 to 7 carbon atoms, or cyclopentyl;
R⁴ represents hydrogen, alkyl having 2 to 5 carbon atoms, alkenyl having 2 to 5 carbon atoms, or alkynyl having 2 to 5 carbon atoms;
Q represents oxygen;
B represents $CH_2$;
R⁵ represents hydrogen, alkyl having 1 to 6 carbon atoms,
or R⁵ represents alkanoyl having 2 to 4 carbon atoms, or $(CH_2)Y—CO_2R^8$ wherein Y is 0 to 4 and R⁸ is hydrogen or alkyl having 1 to 6 carbon atoms;
R⁶ represents hydrogen; and
A represents $—Z—CO_2R^7$ wherein R⁷ represents hydrogen or alkyl having 1 to 6 carbon atoms, and wherein Z is absent or represents straight or branched chain alkylene or alkenylene having up to 6 carbon atoms.

2. A compound according to claim 1 of the formula

[Structure similar to above]

wherein
R¹ represents alkyl having 2–4 carbon atoms;
R² represents methyl or ethyl;
R³ represents alkyl having 1 to 3 carbon atoms;
W represents $(CH_2)_x$ where x is 3 to 5, alkenylene having 3 to 5 carbon atoms, alkynylene having 3 to 5 carbon atoms, or cyclopentyl;
R⁴ represents alkyl having 2 to 4 carbon atoms;
R⁵ represents hydrogen, alkyl having 1 to 4 carbon atoms;
R⁶ represents hydrogen; and
A represents $—Z—CO_2R^7$, wherein R⁷ represents hydrogen or alkyl having 1 to 4 carbon atoms, and wherein Z is absent or represents alkylene having up to 2 carbon atoms; or a stereoisomer or pharmaceutically acceptable salt thereof.

3. A compound according to claim 2 of the formula

[Structure with methoxy, acetyl, propyl substituents, connected via $O—(CH_2)_x—O$ linker to chroman-type ring with R⁵ and A]

wherein
x is 3 to 5, R⁵ represents hydrogen or alkyl of 1 to 4 carbon atoms and A represents $—Z—CO_2R^7$ wherein R⁷ represents hydrogen or alkyl having 1 to 4 carbon atoms and Z is absent or represents alkylene having up to 2 carbon atoms; or a stereoisomer or a pharmaceutically acceptable salt thereof.

4. A compound according to claim 3 of the formula

[Structure with $O—(CH_2)_3—O$ linker and $(CH_2)_p—COOH$ substituent on chroman ring]

wherein p is 0 to 2; or a pharmaceutically acceptable salt thereof.

5. A compound according to claim 4 which is

[Specific compound structure with $O(CH_2)_3O$ linker and $CO_2H$ on chroman ring]

or a pharmaceutically acceptable salt thereof.

6. A pharmaceutical composition comprising an effective anti-inflammatory amount of a compound of claim 1 in a pharmaceutical carrier.

7. A pharmaceutical composition comprising an effective anti-inflammatory amount of a compound of claim 2 in a pharmaceutical carrier.

8. A pharmaceutical composition comprising an effective anti-inflammatory amount of a compound of claim 5 in a pharmaceutical carrier.

9. An orally acceptable pharmaceutical composition of claim 8.

10. A method of treating inflammatory diseases characterized by the production of leukotriene B₄ comprising administering to a mammal in need of anti-inflammatory treatment a therapeutically effective anti-inflammatory amount of a compound of claim 5.

11. A method of treating inflammatory diseases characterized by the production of leukotriene B₄, comprising administering to a mammal in need of anti-inflammatory treatment a therapeutically effective anti-inflammatory amount of a compound of claim 1.

12. A method of treating inflammatory diseases characterized by the production of leukotriene B₄, comprising administering to a mammal in need of anti-inflammatory treatment a therapeutically effective anti-inflammatory amount of a compound of claim 2.

13. A method according to claim 11 wherein the inflammatory disease is rheumatoid arthritis.

14. A method according to claim 11 wherein the inflammatory disease is psoriasis.

15. A compound according to claim 2, which is 7-[3-[4-acetyl-2-(cyclopropylmethyl)-3-methoxyphenoxy]-propoxy]-3,4-dihydro-8-propyl-2H-1-benzopyran-2-carboxylic acid.

16. A compound according to claim 2, which is 7-[[3-(4-acetyl-3-methoxy-2-propylphenoxy)cyclopentyl]oxy]-3,4-dihydro-8-propyl-2H-1-benzopyran-2-carboxylic acid.

17. A compound according to claim 2, which is 7-[3-[4-acetyl-3-methoxy-2-(2-propenyl)phenoxy]-propoxy]-3,4-dihydro-8-propyl-2H-1-benzopyran-2-carboxylic acid.

18. A compound according to claim 2, which is 7-[3-(4-acetyl-3-methoxy-2-propylphenoxy)propoxy]-3,4-dihydro-2H-1-benzopyran-2-carboxylic acid.

19. A compound according to claim 2, which is methyl 7-[5-(4-acetyl-3-methoxy-2-propylphenoxy)pentyl]oxy]-3,4-dihydro-8-propyl-2H-1-benzopyran-2-carboxylate.

20. A compound according to claim 2, which is methyl 3,4-dihydro-7-[3-[3-methoxy-4-(2-methyl-1-oxopropyl)-2-propylphenoxy)-propoxy]-8-propyl-2H-b 1-benzopyran-2-carboxylate.

21. A compound according to claim 2, which is ethyl 7-[3-(4-acetyl-3-methoxy-2-propylphenoxy)propoxy]-3,4-dihydro-8-propyl-2H-1-benzopyran-2-yl-propanoate.

22. A compound according to claim 2, which is 7-[[5-(4-acetyl-3-methoxy-2-propylphenoxy)pentyl]oxy]-3,4-dihydro-8-propyl-2H-1-benzopyran-2-carboxylic acid.

23. A compound according to claim 2, which is 3,4-dihydro-7-[3-[3-methoxy-4-(2-methyl-1-oxopropyl)-2-propylphenoxy]propoxy]-8-propyl-2H-1-benzopyran-2-carboxylic acid.

24. A compound according to claim 2, which is 7-[3-(4-acetyl-3-methoxy-2-propylphenoxy)propoxy]-3,4-dihydro-8-propyl-2H-1-benzopyran-2-propanoic acid.

25. A compound according to claim 2, which is 7-[3-(4-acetyl-3-ethoxy-2-propylphenoxy)-propoxy]-3,4-dihydro-8-propyl-2H-1-benzopyran-2-carboxylic acid.

26. A compound according to claim 2, which is methyl 7-[3-(4-acetyl-3-methoxy-2-propylphenoxy)propoxy]-3,4-dihydro-8-propyl-2H-1-benzopyran-2-carboxylate.

27. A pharmacetuical composition comprising an effective anti-inflammatory ammount of a compound selected from the group consisting of
7-[3-[4-acetyl-2-(cyclopropylmethyl)-3-methoxyphenoxy]-propoxy]-3,4-dihydro-8-propyl-2H-1-benzopyran-2-carboxylic acid,
7-[[3-(4-acetyl-3-methoxy-2-propylphenoxy)cyclopentyl]oxy]-3,4-dihydro-8-propyl -2H-1-benzopyran-2-carboxylic acid,
7-[3-[4-acetyl-3-methoxy-2-(2-propenyl)phenoxy]-propoxy-3,4-dihydro-8-propyl-2H-1-benzopyran-2-carboxylic acid,
7-[3-(4-acetyl-3-methoxy-2-propylphenoxy)propoxy-3,4-dihydro-2H-1-benzopyran-2-carboxylic acid,
methyl 7-[[5-(4-acetyl-3-methoxy-2-propylphenoxy)pentyl]-oxy]-3,4-dihydro-8-propyl-2H-1-benzopyran-2-carboxylate,
methyl 3,4-dihydro-7-[3-[3-methoxy-4-(2-methyl-1-oxopropyl)-2-propylphenoxy)-propoxy]-8-propyl-2H-1-benzopyran-2-carboxylate,
ethyl 7-[3-(4-acetyl-3-methoxy-2-propylphenoxy)propoxy]-3,4-dihydro-8-propyl-2H-1-benzopyran-2-propanoate,
7-[[5-(4-acetyl-3-methoxy-2-propylphenoxy)pentyl]oxy]-3,4-dihydro-8-propyl-2H-1-benzopyran-2-carboxylic acid,
3,4-dihydro-7-[3-[3-methoxy-4-(2-methyl-1-oxopropyl)-2-propylphenoxy]propoxy]-8-propyl-2H-1-benzopyran-2-carboxylic acid,
7-[3-(4-acetyl-3-methoxy-2-propylphenoxy)propoxy]-3,4-dihydro-8-propyl-2H-1-benzopyran-2-propanoic acid,
7-[3-(4-acetyl-3-ethoxy-2-propylphenoxy)-propoxy]-3,4-dihydro-8-propyl-2H-1-benzopyran-2-carboxylic acid, and
methyl 7-[3-(4-acetyl-3-methoxy-2-propylphenoxy)propoxy]-3,4-dihydro-8-propyl-2H-1-benzopyran-2-carboxylate
in a pharmaceutical carrier.

28. A method of treating inflammatory diseases characterized by the production of leukotriene B₄ comprising administering to a mammal in need of anti-inflammatory treatment a therapeutically effective anti-inflammatory amount of a compound selected from the group consisting of
7-[3-[4-acetyl-2-(cyclopropylmethyl)-3-methoxyphenoxy]-propoxy]-3,4-dihydro-8-propyl-2H-1-benzopyran-2-carboxylic acid,
7-[[3-(4-acetyl-3-methoxy-2-propylphenoxy)cyclopentyl]oxy]-3,4-dihydro-8-propyl-2H-1-benzopyran-2-carboxylic acid,
7-[3-[4-acetyl-3-methoxy-2-(2-propenyl)phenoxy]-propoxy-3,4-dihydro-8-propyl-2H-1-benzopyran-2-carboxylic acid,
7-[3-(4-acetyl-3-methoxy-2-propylphenoxy)propoxy-3,4-dihydro-2H-1-benzopyran-2-carboxylic acid,
methyl 7-[[5-(4-acetyl-3-methoxy-2-propylphenoxy)pentyl]-oxy]-3,4-dihydro-8-propyl-2H-1-benzopyran-2-carboxylate,
methyl 3,4-dihydro-7-[3-[3-methoxy-(2-methyl-1-oxopropyl)-2-propylphenoxy)-propoxy]-8-propyl-2H-1-benzopyran-2-carboxylate,
ethyl 7-[3-(4-acetyl-3-methoxy-2-propylphenoxy)propoxy]-3,4-dihydro-8-propyl-2H-1-benzopyran-2-propanoate,
7-[[5-(4-acetyl-3-methoxy-2-propylphenoxy)pentyl]oxy]-3,4-dihydro-8-propyl-2H-1-benzopyran-2-carboxylic acid,
3,4-[dihydro-7-[3-[3-methoxy-4-(2-methyl-1-oxopropyl)-2-propylphenoxy]propoxy]-8-propyl-2H-1-benzopyran-2-carboxylic acid,
3-[7-[3-(4-acetyl-3-methoxy-2-propylphenoxy)propoxy]-3,4-dihydro-8-propyl-2H-1-benzopyran-2-yl-propanoic acid,
7-[3-(4-acetyl-3-ethoxy-2-propylphenoxy)-propoxy]-3,4-dihydro-8-propyl-2H-1-benzopyran-2-carboxylic acid, and
methyl 7-[3-(4-acetyl-3-methoxy-2-propylphenoxy)propoxy]-3,4-dihydro-8-propyl-2H-1-benzopyran-2-carboxylate.

* * * * *

UNITED STATES PATENT AND TRADEMARK OFFICE
CERTIFICATE OF CORRECTION

PATENT NO. : 4,889,871

DATED : Dec. 26, 1989

INVENTOR(S) : Djuric et al.

It is certified that error appears in the above-identified patent and that said Letters Patent is hereby corrected as shown below:

Column 4, line 53, reading "-3,4dihydro-" should read
-- -3,4-dihydro- --.
Column 7, line 7, reading "dose ration" should read
-- dose ratio --.
Column 7, line 11, reading "present" should read -- presence --.
Column 14, next to the first structure, -- 4a -- should be inserted to identify the structure.
Column 34, lines 33-34, reading "7-[[4'-(4-acetyl-3-methoxy-2-propylphenoxy)-2-butenyl]]-" should read -- 7-[[4-(4-acetyl-3-methoxy-2-propylphenoxy)-2-butenyl] --.
Column 35, line 3, reading "Afte" should read -- After --.
Column 35, line 68, reading "96.70" should read -- 69.70 --.
Column 37, line 10, reading "prophenyl" should read -- propenyl --
Column 38, line 45, reading "-2H-b 1-" should read
-- -2H-1- --.
Column 47, line 14, reading "atoms 1" should read -- atoms, --.
Column 49, line 35, reading "-2H-b 1-" should read -- -2H-1- --.

Signed and Sealed this

Seventh Day of July, 1992

Attest:

DOUGLAS B. COMER

Attesting Officer

Acting Commissioner of Patents and Trademarks